(12) United States Patent
Choung et al.

(10) Patent No.: US 9,446,061 B2
(45) Date of Patent: Sep. 20, 2016

(54) COMPOSITION CONTAINING ANTIBIOTICS AND LYSOPHOSPHATIDYLCHOLINE FOR BOOSTING IMMUNITY OR TREATMENT OF BACTERIAL INFECTIONS

(75) Inventors: Jai Jun Choung, Gyeonggi-do (KR); Sae Kwang Ku, Daegu (KR); Dong Keun Song, Gangwon-do (KR)

(73) Assignee: ARIMED INC., Seoul (KR)

(*) Notice: Subject to any disclaimer, the term of this patent is extended or adjusted under 35 U.S.C. 154(b) by 0 days.

(21) Appl. No.: 14/128,688

(22) PCT Filed: Jun. 22, 2012

(86) PCT No.: PCT/KR2012/004942
§ 371 (c)(1),
(2), (4) Date: Jan. 23, 2014

(87) PCT Pub. No.: WO2012/177075
PCT Pub. Date: Dec. 27, 2012

(65) Prior Publication Data
US 2014/0134210 A1     May 15, 2014

(30) Foreign Application Priority Data
Jun. 23, 2011   (KR) .................. 10-2011-0061316

(51) Int. Cl.
*A61K 45/06* (2006.01)
*A61K 31/661* (2006.01)
*A61K 31/685* (2006.01)

(52) U.S. Cl.
CPC ........... *A61K 31/685* (2013.01); *A61K 31/661* (2013.01); *A61K 45/06* (2013.01)

(58) Field of Classification Search
CPC ... A61K 45/06; A61K 31/661; A61K 31/685
See application file for complete search history.

(56) References Cited

U.S. PATENT DOCUMENTS

| | | | |
|---|---|---|---|
| 5,350,753 A | 9/1994 | Klesel et al. | |
| 6,165,997 A * | 12/2000 | Cohen et al. | ................. 514/148 |
| 7,410,955 B2 * | 8/2008 | Kim et al. | ........................ 514/77 |
| 2005/0042202 A1 | 2/2005 | Weiner et al. | |
| 2005/0288254 A1 * | 12/2005 | Kim et al. | ....................... 514/78 |
| 2010/0286093 A1 | 11/2010 | Kim et al. | |

FOREIGN PATENT DOCUMENTS

KR    10-2004-0017613 A  *  2/2004

OTHER PUBLICATIONS

English Translation of KR 10-2004-0017613 A (Feb. 24, 2004), Machine translated on Mar. 25, 2015.*

* cited by examiner

*Primary Examiner* — James D Anderson
(74) *Attorney, Agent, or Firm* — Vorys, Sater, Seymour & Pease LLP; Mih Suhn Koh

(57) ABSTRACT

The present invention relates to: a pharmaceutical composition containing lysophosphatidylcholine or analogs thereof and antibiotics as active ingredients for boosting immunity or the treatment of bacterial infections; a method for boosting immunity or the treatment of bacterial infections, which comprises a step for administering the composition; and a kit containing the composition for boosting immunity or the treatment of bacterial infections.

4 Claims, 16 Drawing Sheets

COMPOSITION CONTAINING ANTIBIOTICS AND LYSOPHOSPHATIDYLCHOLINE FOR BOOSTING IMMUNITY OR TREATMENT OF BACTERIAL INFECTIONS

CROSS REFERENCE TO RELATED APPLICATIONS AND CLAIM OF PRIORITY

This patent application is a National Phase application under 35 U.S.C. §371 of International Application No. PCT/KR2012/004942, filed Jun. 22, 2012, which claims priority to Korean Patent Application No. 10-2011-0061316 filed Jun. 23, 2011, entire contents of which are incorporated herein by reference.

BACKGROUND

1. Technical Field

The present invention relates to pharmaceutical compositions for enhancement of immunity or treatment of bacterial infections, containing lysophosphatidylcholine or analogs thereof and antibiotics, as active ingredients; a method for enhancement of immunity or treatment of bacterial infections, including dosing the composition; and a kit for enhancement of immunity or treatment of bacterial infections, containing the composition.

2. Description of the Related Art

Bacterial infections are diseases caused by bacteria or viruses which invade and live in blood, body fluid, and tissues, and become a major threat to humans due to a lack of development of new antibiotics and an increase in antibiotic-resistant microorganisms. The bacterial infections are peritonitis, pneumonia, osteomyelitis, cellulitis, meningitis, nephritis, enteritis, gastritis, esophagitis, duodenitis, colitis, and sepsis. The bacterial infections may cause a neutropenic fever in which the immune system does not properly respond to infection or may be accompanied by a fever without a reduction of neutrophils against infection when the immune system is inhibited (for example, in patients with immunodeficient disease such as AIDS, or with immunosuppressant treatment). The bacterial infections become increasingly difficult to treat due to the increased expression of antibiotic-resistant bacteria.

Sepsis is a major cause of death in intensive care units, accounting for over 200,000 deaths per year in the United States alone [Hoyert et al., 1994]. Increasing evidence suggests that sepsis impairs immune function by inducing defects in innate immunity and excessive lymphocyte apoptosis. The resulting immunosuppression has been suggested to be a major contributing factor in sepsis-induced mortality. Accordingly, activation of macrophages with interferon-γ (IFN-γ) in septic patients, blockade of complement-induced neutrophil dysfunction and inhibition of lymphocyte apoptosis in animals with experimentally induced sepsis have all been reported to have beneficial effects [Yan et al., Therapeutic effects of lysophosphatidylcholine in experimental sepsis. Nat. Med. 10:161-167(2004)).

Lysophosphatidylcholine (LPC) is a major component of oxidized low-density lipoprotein. LPC has various stimulatory effects in many types of immune cells in vitro, including monocytes, macrophages, T lymphocytes and neutrophils, and the beneficial effects of LPC on the sepsis have been reported [Yan et al., 2004].

Throughout the entire specification, many papers and patent documents are referenced and their citations are represented. The disclosures of cited papers and patent documents are entirely incorporated by reference into the present specification, and the level of the technical field within which the present invention falls and details of the present invention are explained more clearly.

BRIEF SUMMARY

The present inventors endeavored to develop methods for maximizing therapeutic effects of lysophosphatidylcholine against mass infection. As a result, the present inventors found that effects in enhancement of immunity or treatment of bacterial infections were significantly increased when lysophosphatidylcholine and antibiotics were used in combination than when used alone, and then completed the present invention.

Accordingly, an aspect of the present invention is to provide a composition for enhancement of immunity or treatment of bacterial infections.

Another aspect of the present invention is to provide a method for enhancement of immunity or treatment of bacterial infections.

Still another aspect of the present invention is to provide a kit for enhancement of immunity or treatment of bacterial infections.

Other purposes and advantages of the present disclosure will become clarified by the following detailed description of invention, claims, and drawings.

In accordance to an aspect of the present invention, there is provided a pharmaceutical composition for enhancement of immunity or treatment of bacterial infections, the composition containing, as active ingredients, (i) lysophosphatidylcholine or an analog thereof, and (ii) an antibiotic.

The present inventors endeavored to develop methods for maximizing therapeutic effects of lysophosphatidylcholine against mass infection. As a result, the present inventors found that effects in enhancement of immunity or treatment of bacterial infections were significantly increased when lysophosphatidylcholine and antibiotics were used in combination than when used alone.

As used herein, the term "lysophosphatidylcholine or analog(s) thereof" generally refers to phosphatidylcholine analog(s) in which one fatty acid group is removed from phosphatidylcholine by partial hydrolysis of phosphatidylcholine through enzymatic action of phospholipase. The present invention includes, without limitation, lysophosphatidylcholine and analogs thereof, which have effects in enhancement of immunity and treatment of bacterial infections through the enhancement of immunity when being used in combination with antibiotics.

According to a preferable embodiment of the present invention, the lysophosphatidylcholine may be a compound represented by Chemical Formula 1 below, and the analog thereof may be a compound represented by Chemical Formula 2:

Chemical Formula 1

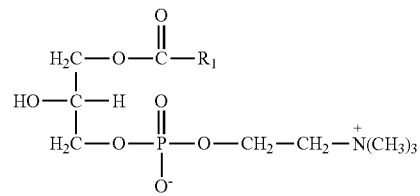

wherein, $R_1$ is $C_{4-30}$ alkyl, or $C_{4-30}$ alkenyl having one or more double bonds; and

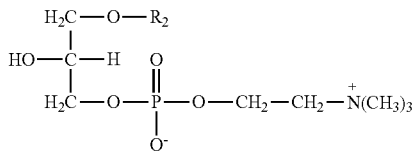

Chemical Formula 2 wherein, $R_2$ is $C_{4-30}$ alkyl, or $C_{4-30}$ alkenyl having one or more double bonds.

Preferably, the compound of Chemical Formula 1 may be selected from the group consisting of L-α-lysophosphatidylcholine, stearoyl; L-α-lysophosphatidylcholine, myristoyl; L-α-lysophosphatidylcholine, palmitoyl; DL-α-lysophosphatidylcholine, palmitoyl; and L-α-lysophosphatidylcholine, oleoyl.

Preferably, the compound of Chemical Formula 2 may be selected from the group consisting of L-α-lysophosphatidylcholine, γ-O-alk-1-enyl; L-α-lysophosphatidylcholine, γ-O-alkyl; DL-α-lysophosphatidylcholine, γ-O-hexadecyl; and L-α-lysophosphatidylcholine, γ-O-hexadecyl.

Since lysophosphatidylcholine and analogs thereof are materials in the mammalian body, the safety of lysophosphatidylcholine and analogs thereof is almost proved.

Preferably, the lysophosphatidylcholine of the present invention also includes isomers thereof. According to an embodiment of the present invention, it was confirmed that effects in enhancement of immunity and treatment of bacterial infections were more favorable when lysophosphatidylcholine isomers and antibiotics are used in combination than when used alone (Tables 4 and 5).

As used herein, the term "antibiotics" refers to metabolic substances produced by microbial organisms, which inhibit or destroy growths of other microorganisms even in small quantities, and the term encompasses both naturally occurring and chemically synthesized antibiotic materials. Considering purposes of the present invention, the antibiotics of the present invention include, without limitation, any antibiotic that can maximize the effects in enhancement of immunity or treatment of bacterial infections of lysophosphatidylcholine or analogs thereof by being dosed in combination with lysophosphatidylcholine or analogs thereof.

Preferably, the antibiotic may be selected from the group consisting of carbapenem-based antibiotics, cephalosporin-based antibiotics, glycopeptides-based antibiotics, penicillin-based antibiotics, quinolone-based antibiotics, serine protease-based antibiotics, polymyxin-based antibiotics, aminoglycoside-based antibiotics, bacteriostatic antibiotics, and a combination thereof.

Preferably, the carbapenem-based antibiotics may include doripenem; the cephalosporin-based antibiotics may include ceftriaxone sodium; the glycopeptides-based antibiotics may include vancomycin hydrochloride; the penicillin-based antibiotics may include potassium benzylpenicillin; the quinolone-based antibiotics may include DW286 (7-[3-(aminomethyl)-4-(methoxyimino)-3-methyltetrahydro-1H-1-pyrrolyl]-1-cyclopropyl-6-fluoro-4-oxo-1,4-dihydro[1,8] naphthyridine-3-carboxylic acid hydrochloric acid salt) or ciprofloxacin hydrochloride hydrate; the serine protease-based antibiotics may include drotrecogin alfa (activated); the polymyxin-based antibiotics may include colistin; the aminoglycoside-based antibiotics may include tobramycin; and the bacteriostatic antibiotics may include fusidic acid.

In the present invention, the ratios of the lysophosphatidylcholine or analogs thereof and the antibiotics, which are included in the composition of the present invention, may be determined depending on the types of antibiotics.

According to a preferable embodiment of the present invention, the weight ratios between the lysophosphatidylcholine or analogs thereof and the antibiotics, which are included in the composition of the present invention, may be 1:0.1-45, preferably 1:0.2-45, more preferably 1:0.3-45, still more preferably 1:0.4-45, and still more preferably 1:0.5-45.

According to a more preferable embodiment of the present invention, the weight ratios between the lysophosphatidylcholine or analogs thereof and the antibiotics, which are included in the composition of the present invention, may be 1:0.1-44, preferably 1:0.2-44, more preferably 1:0.3-44, still more preferably 1:0.4-44, and still more preferably 1:0.5-44.

According to a more preferable embodiment of the present invention, the weight ratios between the lysophosphatidylcholine or analogs thereof and the antibiotics, which are included in the composition of the present invention, may be 1:0.1-43, preferably 1:0.2-43, more preferably 1:0.3-43, still more preferably 1:0.4-43, and still more preferably 1:0.5-43.

According to a more preferable embodiment of the present invention, the weight ratios between the lysophosphatidylcholine or analogs thereof and the antibiotics, which are included in the composition of the present invention, may be 1:0.1-42, preferably 1:0.2-42, more preferably 1:0.3-42, still more preferably 1:0.4-42, and still more preferably 1:0.5-42.

According to a more preferable embodiment of the present invention, the weight ratios between the lysophosphatidylcholine or analogs thereof and the antibiotics, which are included in the composition of the present invention, may be 1:0.1-41, preferably 1:0.2-41, more preferably 1:0.3-41, still more preferably 1:0.4-41, and still more preferably 1:0.5-41.

According to a more preferable embodiment of the present invention, the weight ratios between the lysophosphatidylcholine or analogs thereof and the antibiotics, which are included in the composition of the present invention, may be 1:0.1-40, preferably 1:0.2-40, more preferably 1:0.3-40, still more preferably 1:0.4-40, and still more preferably 1:0.5-40.

As used herein, the term "DW286" may be used interchangeably with "DW286AA" or "DW286aa".

According to a preferred embodiment of the present invention, the weight ratios between DW286 and lysophosphatidylcholine or analogs thereof, which are included in the composition of the present invention, may be 1:0.1-5, preferably 1:0.2-5, more preferably 1:0.3-5, still more preferably 1:0.4-5, still more preferably 1:0.5-5, still more preferably 1:0.6-5, still more preferably 1:0.7-5, still more preferably 1:0.8-5, still more preferably 1:0.9-5, still more preferably 1:1-5, still more preferably 1:1-4, still more preferably 1:1-3, and still more preferably 1:2.

The present invention is directed to a composition exhibiting a synergistic effect in enhancement of immunity or treatment of bacterial infections by dosing antibiotics and lysophosphatidylcholine or analogs thereof in combination. The term "synergistic effect" refers to, when combining two or more agents, producing an effect greater than the sum of their individual effects or an unexpected effect different therefrom. The term "combining" refers to simultaneous dosing of a mixture of two or more agents or sequential dosing of their individual agents.

In an example of the present invention, in order to investigate effects in enhancement of immunity and treatment of bacterial infections by the dosing of LPC and DW286 in combination, Mix group (LPC:DW286 2:1), LPC-DW286 group (LPC pre-dosing and DW286 dosing group), DW286-LPC group (DW286 pre-dosing and LPC dosing), LPC alone dosing group, and DW286 alone dosing group were evaluated on cyclophosphamide-cecal ligation and puncture (CPA-CLP)-induced sepsis mice and CPA-treated immunosuppressive and/or mutagenic mice. As a result, increased effects in enhancement of immunity and treatment of bacterial infections were observed in the Mix, LPC-DW286, and DW286-LPC groups, which are for the dosing of antibiotics and LPC in combination, and the greatest effects in enhancement of immunity and treatment of bacterial infections were observed in the DW286-LPC group (Table 13). Further, when, besides DW286, ciprofloxacin hydrochloride hydrate, potassium benzylpenicillin, ceftriaxone sodium, doripenem, vancomycin hydrochloride or drotrecogin alfa (activated), colistin, tobramycin, and fusidic acid each were dosed in combination with LPC, more increased effects in enhancement of immunity and treatment of bacterial infections were detected as compared with when LPC was dosed alone (Tables 6 to 9).

Specifically, as a result of measurement of mortalities in the mouse models, the high survival rate was detected in the DW286-LPC group (Tables 12 and 13). As a result of observation of the organ weight changes (thymus and spleen), the DW286-LPC group effectively inhibited the decreases in lymphoid cells induced by CPA dosing (Table 15). Further, as a result of observation of changes in blood white blood cell (WBC) numbers, significant increases in WBC numbers were observed in only the DW286-LPC group (Table 16), and the changes in WBC differential counts were more favorable in the DW286-LPC group than the LPC alone dosing group. As a result of measurement of changes associated with decreases in lymphoid cells and dramatical splenic atrophy, the DW286-LPC group showed the high inhibition trend (Table 18) on the decreases in lymphoid cells and splenic atrophy as compared with other groups (FIGS. 7 and 8). Further, as a result of Immunohistochemical observation of thymus and spleen, CPA caused the decreases of CD3+, CD4+, CD8+, and TNF-α+ cells in spleen and thymus. However, it was observed that the decreases in these cells induced by CPA dosing were comparatively inhibited when LPC was used and DW286 and LPC were dosed in combination. More favorable effects were observed in the DW286-LPC group as compared with when LPC was dosed alone (Table 19). It can be seen from these results that the combinational agents of the present invention have effects in enhancement of immunity or treatment of bacterial infections through enhancement of immunity.

As used herein, the term "bacterial infections" refers to diseases that are caused by direct/indirect effects from in vivo invasion of bacteria but can be treated through enhancement of immunity. The term encompasses various diseases, such as a fever in patients with immunodeficient disease, such as AIDS, or with immunosuppressant treatment even without a reduction of neutrophils infected after the immune system is inhibited, resistances to antibiotics, and the like.

Preferably, the bacterial infections of the present invention include peritonitis, pneumonia, osteomyelitis, cellulitis, meningitis, nephritis, carditis, enteritis, gastritis, esophagitis, duodenitis, colitis, and sepsis. In an example of the present invention, peritonitis was induced by cecal ligation and puncture (CPL). In an example of the present invention, CLP and cyclophosphamide.$H_2O$(CPA) were used to investigate effects in enhancement of immunity or treatment of bacterial infections of the combinational agents of the present invention. Since CPA is a material inhibiting an immune response of the immune system, it can be seen that the compositions of the present invention have effects even in the diseases caused by suppressed immune responses (or deficient immune functions).

As used herein, the term "immunity" refers to a self-defense system in the animal body and a biological phenomenon in which various envading materials or organisms are distinguished from the organism's own tissues and then these invaders are eliminated.

As used herein, the term "enhancement of immunity" refers to increasing specific or non-specific, cellular and/or humoral immune responses of hosts. The compositions of the present invention exhibit effects in enhancement of immunity even in an immunosuppressed state by dosing antibiotics and LPC or analogs thereof in combination, and finally the compositions of the present invention are useful in treatment of bacterial infections through this enhancement of immunity.

The compositions of the present invention include pharmaceutical acceptable carriers, and may be formulated for the human body or veterinary medicine.

A pharmaceutical composition for oral administration may be presented as a separate unit, for example, capsule or tablet; powder or granule; solvent, syrup, or suspension (in aqueous or non-aqueous liquid; edible foaming or whip; an emulsion).

An excipient suitable for the tablet or hard gelatin capsule may include lactose, corn starch and derivatives thereof, and stearic acid and salts thereof. An excipient suitable for the soft gelatin capsule may include, for example, vegetable oil, wax, fat, semi-solid, and liquid polyol. An excipient usable to prepare the solvent and syrup may include, for example, water, polyol, and sugar. For preparation of the suspension, oil-in-water or water-in-oil suspension may be provided using oil (for example, vegetable oil). A pharmaceutical composition adapted for transdermal dosing may be presented as a separate patch for being closely contacted with the skin of a receiver for a long time.

A pharmaceutical composition for parenteral dosing includes aqueous and non-aqueous sterile injections which may contain anti-oxidants, buffers, bacteriostats, and solutes (rendering the formulation substantially isotonic with the blood of the intended recipient); and aqueous and non-aqueous sterile suspensions which may contain suspending agents and thickening agents. An excipient usable in the injections may include, for example, water, alcohol, polyol, glycerin, and vegetable oil. The pharmaceutical compositions may be presented in unit-dose or multi-dose containers, for example sealed ampoules and vials, and may be stored in a freeze-dried (lyophilised) condition requiring only the addition of the sterile liquid carrier, for example water for injections, immediately prior to use. Ready-to-used injection and suspension may be prepared from sterile powders, granules, and tablets.

In accordance to another aspect of the present invention, there is provided a method for enhancement of immunity or treatment of bacterial infections, the method including, dosing a subject with (i) lysophosphatidylcholine or an analog thereof, and (ii) an antibiotic.

In the method for treatment of the present invention, the lysophosphatidylcholine or analogs thereof, antibiotics, enhancement of immunity, and bacterial infections are as described above. Therefore, the overlapping descriptions are omitted to avoid excessive complication of the specification due to repetitive descriptions thereof.

According to an embodiment of the present invention, the materials may be dosed in combination such that (i) the lysophosphatidylcholine or analogs thereof, and (ii) the antibiotics may be simultaneously or sequentially dosed, depending on the types of antibiotics. The dosing interval may be determined depending on factors including patient's disease type and severity, age, sex, drug activity, drug sensitivity, dosing time, dosing route and excretion ratio, duration of treatment, and concurrently used medications, and other factors well-known in the medical field. In addition, the antibiotics and/or the lysophosphatidylcholine or analogs thereof may be dosed several times when they are sequentially dosed.

Preferably, when the antibiotic of the present invention is DW286, DW286 may be pre-dosed and then lysophosphatidylcholine or analogs thereof may be dosed.

In an example of the present invention, as a result of evaluation of the Mix group (LPC:DW286 2:1), LPC-DW286 group (LPC pre-dosing and DW286 dosing group), DW286-LPC group (DW286 pre-dosing and LPC dosing group), LPC alone dosing group, and DW286 alone dosing group on CPA-CLP sepsis mice and CPA-induced immunosuppressive and/or CPA-treated immunosuppressive and/or mutagenic mice, the increased effects in enhancement of immunity and treatment of bacterial infections can be observed in the antibiotics and LPC composition group as compared with the alone dosing groups. The highest effects in enhancement of immunity and treatment of bacterial infections can be detected in the DW286-LPC group, which is the DW286 pre-dosing and LPC dosing group, rather than the LPC-DW286 group, which is the LPC pre-dosing and DW286 dosing group.

As used herein, the term "subject" refers to, but is not limited to, mammals such as humans, cattle, horses, sheep, pigs, goats, camels, antelope, and dogs, which are in need of enhancement of immunity, suffering from bacterial infections, or at risk for bacterial infections. Immunity can be enhanced and bacterial infections can be treated by dosing a subject with the antibiotics and the lysophosphatidylcholine or analogs thereof of the present invention.

As used herein, the term "dosing" refers to introducing a predetermined material into a subject in any appropriate manner, and the dosing may performed through any general route through which the material can reach target tissues. The dosing may be performed through routes including, but are not limited to, intraperitoneal, intravenous, intramuscular, subcutaneous, intradermal, oral, topical, intranasal, intrapulmonary, and rectal routes. In addition, the pharmaceutical composition may be dosed by any device that can deliver active ingredients to target cells.

The lysophosphatidylcholine or analogs thereof and antibiotics of the present invention may be dosed in a therapeutically effective amount.

As used herein, the term "therapeutically effective amount" refers to an amount that is sufficient to treat diseases at a reasonable benefit-risk ratio, which is applicable to medical treatment. The level of effective amount may be determined depending on factors including patient's disease type and severity, age, sex, drug activity, drug sensitivity, dosing time, dosing route and excretion ratio, duration of treatment, and concurrently used medications, and other factors well-known in the medical field. Single or multiple dosing of the materials may be performed. Considering the above factors, it is important that the dosing is performed such that the maximum effect can be obtained with the minimum amount without side effects, and such an amount may be easily determined by those skilled in the art.

In accordance to still another embodiment of the present invention, there is provided a kit for enhancement of immunity or treatment of bacterial infections, the kit including (i) lysophosphatidylcholine or an analog thereof, and (ii) an antibiotic, which are contained in a single container or individual containers.

In the kit of the present invention, the lysophosphatidylcholine or analog thereof, the antibiotic, enhancement of immunity, and bacterial infections are as described above. Therefore, the overlapping descriptions are omitted to avoid excessive complication of the specification due to repetitive descriptions thereof.

According to an embodiment of the present invention, appropriate amounts of lysophosphatidylcholine or analogs thereof and antibiotics may be stored in separate containers in the kit of the present invention. Further, the kit of the present invention may include a pharmaceutically acceptable carrier, and instructions for the use of the kit. The instructions may include a mixing method of the LPC or analog thereof and the antibiotic for enhancement of immunity or treatment of bacterial infections; the dosing order or dosing method of the antibiotic followed by the LPC or analog thereof; or the dosing order of the LPC or analog thereof followed by the antibiotic.

Features and advantages of the present invention are summarized as follows:

(1) According to the present invention, the dosing of lysophosphatidylcholine or analogs thereof in combination with antibiotics can lead to synergistic effects in enhancement of immunity or treatment of bacterial infections.

(2) The present invention can by usefully used in treatment of diseases in which the immune system is inhibited through infection and diseases in which the immune system is inhibited after infection, thereby significantly increasing therapeutic effects of the existing antibiotics and lysophosphatidylcholine.

DETAILED DESCRIPTION

Figure 1:
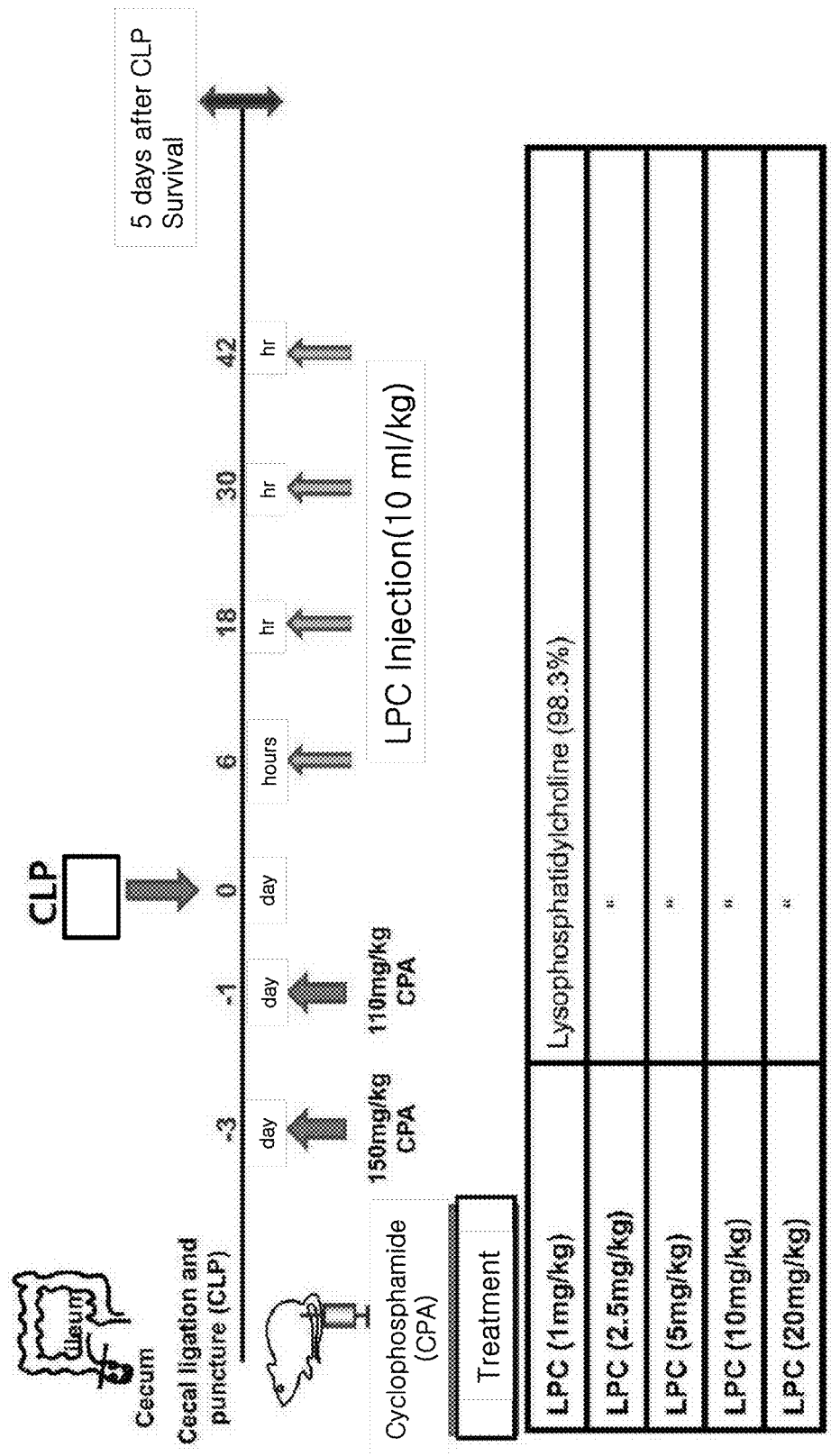
FIG. 1 schematically shows dosing groups and dosing orders of LPC in the CPA-CLP-induced model.

Hereinafter, the present invention will be described in detail with reference to examples. These examples are only for illustrating the present invention more specifically, and it will be apparent to those skilled in the art that the scope of the present invention is not limited by these examples.

EXAMPLES

Example 1

Preparation of Experimental Materials and Animals

DW286 ([7-[3-(aminomethyl)-4-(methoxyimino)-3-methyltetrahydro-1H-1-pyrrolyl]-1 cyclopropyl-6 fluoro-4-oxo-1,4-dihydro[1,8]naphthyridine-3-carboxylic acid hydrochloric acid salt], Lpt, 20021) is a novel fluoro-naphthyridine antibiotic synthesized by Dong Wha Pharm. Inc. (Anayang, Korea). Lysophosphatidylcholine (LPC; 18:0, 94%, GmbH PHOSPHOLIPID, Germany) was used. LPC isomers, that is, 1-oleoyl-2-hydroxy-sn-glycero-3-phosphocholine (1-oleoyl; 18:1 LPC), ciprofloxacin hydrochloride hydrate (Cipro), potassium benzylpenicillin (Peni), ceftriaxone sodium (Ceft), doripenem (Dori), vancomycin hydrochloride (Vanco), drotrecogin alfa (activated) (Xigris), colistin, tobramycin, and fusidic acid (Fusidin) were respectively purchased from Sigma, etc. LPC, DW286, ciprofloxacin hydrochloride hydrate, potassium benzylpenicillin, ceftriaxone sodium, doripenem, vancomycin hydrochloride, and drotrecogin alfa (activated) were stored in a decicator for protection from light and humidity degeneration.

ICR mice (6-wk old, SLC, Japan) were used after acclimatization for 7 or 8 days. Animals were allocated five or four per polycarbonate cage in a temperature (20-25) and humidity (40-450) controlled room. Light:dark cycle was 12 hr:12 hr, and feed (Samyang, Korea) and water were supplied free to access. The experiments were divided to cyclophosphamide-cecal ligation and puncture (CPA-CLP) and cyclophosphamide (CPA) induced immunosuppressive mouse models. All laboratory animals were treated according to the Guide for the Care and Use of Laboratory Animals by Institute of Laboratory Animal Resources, Commission on Life Science, National Research Council, USA on 1996, Washington D.C.

Example 2

Preparation of Animal Models 2-1. Preparation of CPA-Induced Immunosuppressive Mouse Model To induce immunosuppression, 150 mg/kg and 110 mg/kg of CPA (Sigma, USA) were dissolved in physiological saline, and then single intraperitoneally injected 3 days or 1 day before CLP, respectively. In the INTACT control group, an equal volume of physiological saline was dosed instead of CPA by the same method.

CPA is a widely used anti-neoplasic agent, and used alone or in combination with other products. Since CPA treatment severely injures hematopoietic and lymphoid tissues, the use of CPA as an anticancer drug or in bone marrow transplantation conditioning regimes causes profound leucopenia. CPA is known to be biologically inactive by itself until after biotransformation by microsomal enzymes leading to the production of a number of active metabolites capable of alkylating nucleic acids. CPA damages chromosomes through generation of free-radicals and alkylation of DNA, thereby producing mutagenicity. CPA-induced immunosuppressive and/or mutagenic mouse models are valuable animal models for detecting anti-mutagenic or favorable immunomodulatory effects Further, CPA treatment induces the leukopenia and immunosuppression, thereby severely decreasing thymic and splenic T cells, especially CD4 and CD8 cells while reducing various cytokines including TNF-$\alpha$ positive cells.

2-2. Preparation of CPA-CLP Mouse Model

To induce immunosuppression, 150 mg/kg and 110 mg/kg of CPA (Sigma, USA) were dissolved in saline, and then single intraperitoneally injected at 10 ml/kg (of body weight), 3 days or 1 day before CLP, respectively, to booster polymicrobial infections. CPA is well known as an immunosuppressive agent. As described above, CPA treatment followed by CLP was performed for a mouse model for massive infections. For CLP, mice were anesthetized with ketamine hydrochloride (ICN Biochemicals Inc., USA) and xylazine hydrochloride (Wako Pure Chemical Industries Ltd., Japan), and a abdominal incision was made to expose the cecum. The exposed cecum was doubly ligated below the ileocecal valve, and punctured twice with a 22-gauge needle. Then, the abdomen was closed following the general procedure. In the INTACT control and CPA control groups, the cecum was exposed and then the abdomen was closed. In the INTACT control group, an equal volume of physiological saline was dosed instead of CPA by the same method.

CLP model, which closely mimics human acute peritonitis, has been regarded as the most clinically relevant animal model of sepsis and valuable animal model for detecting ant-septic effects (Urbaschek and Urbaschek, 1987; Yan et al. 2004; Ghiselli et al. 2006; Wirtz et al. 2006). CLP model mirrors more closely the clinical course of human abdominal sepsis, and an endogenous septic focus causes a polymicrobial infection with the systemic inflammatory response syndrome (Wichterman et al. 1980; Zantl et al. 1998; Maier et al. 2000; Emmanuilidis et al. 2001).

Example 3

Methods 3-1. CPA-Induced Immunosuppress

To induce immunosuppress, 150 and 110 mg/kg of CPA (Sigma, USA) were dissolved in saline and single intraperitoneally injected at 3 or 1 day before CLP or initial test formula dosing, respectively. In Intact control animals, equal volume of saline was only dosed instead of CPA with same methods.

3-2. CLP

For CLP, mice were anesthetized with xylene and ketamine, a small abdominal midline incision was made, and the cecum was exposed. The cecum was mobilized and ligated below the ileocecal valve, punctured through both surfaces twice with a 22-gauge needle, and the abdomen was closed. Mice subjected to intact and CPA controls sham CLP underwent the same procedure, except for ligation and puncture of the cecum. CLP was conducted 1 day after second dose of CPA.

3-3. Measurement of Body Weight and Mortalities

In CPA-CLP model, body weight and mortalities were measured once a day for 5 days with automatic electronic balances (Sartorius Co., Ltd., USA), once a day for 2 days in CPA-treated model. All animals were overnight fasted at CPA dosing, CLP or initial dosing to reduce differences from feeding. In addition, body weight gains were calculated as follows:

EQUATION 1. Body weight gains (g)

CPA-CLP Model: Body weight at sacrifice—at CLP(5 days)

CPA-Treat Model: Body weight at sacrifice—at initial dosing (2 days)

3-4. Organ Weight Measurement

At sacrifice of CPA-treated model, the wet-weights of spleen and thymus were measured and regarded as absolute weight and then relative organ weight (% of body weight) was calculated as follow:

EQUATION 2. Relative organ weights

=[(Absolute organ weights/Body weight at sacrifice individual)×100]

3-5. Blood Collection and WBC Counts

Blood were collected at sacrifice of CPA-treated model from vena cava and total blood leukocyte numbers were calculated using counting chamber, diluting pipette and Türk solution as dilution solution. All numbers were calculated as $\times 10^3/mm^3$. In addition, cell numbers of lymphocytes, eosinophils, neutrophils, monocytes and basophils were calculated among 100 total leukocytes in smear blood samples stained with Giemsa.

3-6. Bone Marrow Preparation and Recoding of Micronuclei

Bone marrow preparations of CPA-treated model were made according to Schimid [1975]. In brief, bone marrow cells were collected from aforementioned femur in 3 ml of inactivated fetal bovine serum (GIBCO BRL, USA), centrifuged, and smeared on slide. Preparations were dried, and fixed by submerging in absolute methanol (for 10~20 min). Fixed slides were stained as follow:

| | |
|---|---|
| May-Grunwald stain | 3 min |
| May-Grunwald stain (1:1 diluted) | 2 min |
| Giemsa stain (1:6 diluted) | 10 min |

Slides were randomly coded and examined under×1000 magnification by two different experts. Small round or oval shaped bodies, size of which ranging about ⅕ to 1/20 of diameter of PCE, were counted as micronuclei. Attention was given to discriminate micronuclei from artifacts. Results were expressed as the number of MNPCEs in 1000 PCEs. Mean number of MNPCE±S.D. was calculated for each treatment group. In addition, PCE/(PCE+normochromatic erythrocytes (NCE) ratio were also calculated by counting 500 erythrocytes for detecting possibility of cytotoxicity [Heddle et al., 1984].

3-7. Histopathology

After measuring of organ weight, thymus and spleen was sampled. Sampled organs were fixed in 10% neutral buffered formalin. After paraffin embedding, 3-4 μm sections were prepared. Representative sections were stained with Hematoxylin and Eosin (H&E) for light microscopical examination. After that the histological profiles of individual organs were observed.

Histomorphometry—

The numbers of white pulps in spleen were calculated as N/histological sections (×50) using automated image analysis (analySIS Image Processing; SIS, Germany). In addition, the numbers of atrophic changes on thymic cortex/total observed number of thymus were also calculated.

3-8. Immunohistochemistry (IHC)

After deparraffinized, CD3 epitope retrievals were conducted in 10 mM Tris-1 mM EDTA Buffer (pH 9.0), CD4 and CD8 in 1 mM EDTA Buffer (pH 8.0), and TNF-α in 10 mM Citrate Buffer (pH 6.0) as previous methods. Primary anti-antibodies used in the invention were as following table.

TABLE 1

| Anti-serum | Code | Supplier | Dilution rate |
|---|---|---|---|
| Anti-mouse CD3(17A2) monoclonal antibody | CBL-1317 | Chemicon Inc., CA, USA. | 1:100 |
| Anti-mouse CD4(GK1.5) monoclonal antibody | CBL-13583 | Chemicon Inc., CA, USA. | 1:100 |
| Anti-mouse CD8(Ly-2) monoclonal antibody | CBL-1318 | Chemicon Inc., CA, USA. | 1:100 |
| Anti-TNF-a polyclonal antibody | HP8001 | Hycult biotechnology b.v., Netherlands. | 1:100 |

*All antisera were raised in rat.

The water bath with a staining dish, containing a buffer, was preheated until the temperature reached 95-100. The staining dish was placed at room temperature and the slides were cooled for 20 minutes. After epitope retrivals, sections were immunostained as following steps First, the sections were incubated with methanol and 0.3% $H_2O_2$ for 30 min to block endogenous peroxidase activity at room temperature, and then rinsed three times in 0.01M phosphate buffered saline (PBS; pH 7.2) for 3 times. Then, the sections were incubated with the normal horse serum blocking solution (Vector Lab. Inc., CA, USA., dilution 1:100) for 1 hr at room temperature in a humidity chamber, to block non-specific binding of immunoglobulin, and then rinsed three times in 0.01M PBS. The sections were incubated with four types of primary antisera for 12 hrs at 4 in a humidity chamber, and then rinsed three times in 0.01M PBS. The sections were incubated with universal biotinylated secondary antibody for 1 hr at room temperature in a humidity chamber, and then rinsed three times in 0.01M PBS. The sections were incubated with ABC reagents (Vectastain Elite ABC Kit, Vector Lab. Inc., CA, USA. Dilution 1:50) for 1 hr at room temperature in a humidity chamber, and then rinsed three times in 0.01M PBS. The sections were incubated in the peroxidase substrate kit (Vector Lab. Inc., CA) for 30 seconds at room temperature, and then rinsed three times in 0.01M PBS. The sections were counterstained with the Mayer's hematoxylin solution, and then rinsed in running tap water for 30 minutes. The sections were dehydrated through 95% ethanol for 2 min and 100% ethanol for 3 hrs, and then rinsed in xylene for 2 hrs. After that, the sections were observed using a cover slip with permanent mounting medium under the light microscope (Zeiss, Germany).

Histomorphometry—Among 1000 splenic or thymic cells, the numbers (N) of immunoreactive cells (CD3+, CD4+, CD8+, and TNF-α+) were observed as N/1000 splenocytes or thymocytes using automated image analysis. In thymus, the counts were conducted in the both cortex and medulla separately.

3-9. Statistical Analyses

Mean and standard deviations (Mean±S.D.) were calculated. Statistical analyses were conducted using Mann-Whitney U-Wilcoxon Rank Sum W test (MW test) with SPSS for Windows (Release 6.1.3., SPSS Inc., USA). To help the understanding of the efficacy of test materials on differences between intact and CPA controls, and CPA control and test groups in CPA-treated model as follows:

EQUATION 3. Percentage Changes vs intact control (%)
=[((Data of CPA control−Data of intact control)/Data of intact control)×100]

EQUATION 4. Percentage Changes vs CPA control (%)
=[((Data of test groups−Data of CPA control)/Data of CPA control)×100]

Example 4

Effects of LPC Concentrations on Survivabilities in CPA-CLP-Induced Mouse Model

Efficacies depending on different doses of LPC were investigated by using CPA-induced immunosuppressive and then CLP-induced sepsis mice. CPA-induced immunosuppressive and CLP-induced sepsis mice were subcutaneously dosed with five doses of LPC (1, 2.5, 5, 10, and 20 mg/kg), 4 times 12-hr intervals from 6 hrs after CLP, respectively. Then, body weight and mortality changes were observed. LPC was dissolved in 5% human albumin (Green Cross, KOREA), and dosed at 10 ml/kg (of body weight) for each. The dosing orders and dosing groups were schematically represented in FIG. 1.

Specifically, ICR mice (6-wk old male, SLC, Japan) were divided into seven groups (ten mice per group), CPA control group (CPA-treated sham CLP operated vehicle dosing group), CPA-CLP control group (CPA-treated CLP operated vehicle dosing group), LPC 1 mg/kg-dosing group after CPA-CLP, LPC 2.5 mg/kg-dosing group after CPA-CLP, LPC 5 mg/kg-dosing group after CPA-CLP, LPC 10 mg/kg-dosing group after CPA-CLP, and LPC 20 mg/kg-dosing group after CPA-CLP. Test materials were subcutaneously dosed at 10 ml/kg (of body weight), 4 times 12-hr intervals by using 5% human serum albumin as vehicle. That is, five doses of LPC were subcutaneously dosed, 4 times 12-hr intervals from 6 hrs after CLP. LPC was dissolved in 5% human serum albumin (Green Cross, KOREA), and dosed at 10 ml/kg (of body weight) for each. In the Sham and CLP control groups, 10 ml/kg of only 5% human serum albumin was subcutaneously dosed at the same intervals. After dosing, body weight and mortality changes were observed by the procedure as described in Example 3-3.

TABLE 2

Effects of LPC on mortalities in CPA-CLP sepsis mouse mode (SEP008)

| Mortalities | Controls | | LPC | | | | |
| --- | --- | --- | --- | --- | --- | --- | --- |
| | CPA | CPA + CLP | 1 mpk | 2.5 mpk | 5 mpk | 10 mpk | 20 mpk |
| $1^{st}$ CPA treat | 0/10 | 0/10 | 0/10 | 0/10 | 0/10 | 0/10 | 0/10 |
| $2^{nd}$ CPA treat | 0/10 | 0/10 | 0/10 | 0/10 | 0/10 | 0/10 | 0/10 |
| At CLP (day 0) | 0/10 | 0/10 | 0/10 | 0/10 | 0/10 | 0/10 | 0/10 |
| Day 1 | 0/10 | 6/10 | 4/10 | 2/10 | 4/10 | 1/10 | 1/10 |
| Day 2 | 0/10 | 4/4 | 2/6 | 2/8 | 1/6 | 2/9 | 1/9 |
| Day 3 | 0/10 | 0/0 | 2/4 | 3/6 | 1/5 | 1/7 | 2/8 |
| Day 4 | 0/10 | 0/0 | 2/2 | 2/3 | 1/4 | 1/6 | 2/6 |
| Day 5 | 0/10 | 0/0 | 0/0 | 1/1 | 0/3 | 1/5 | 2/4 |
| Day 6 | 0/10 | 0/0 | 0/0 | 0/0 | 2/3 | 2/4 | 0/2 |
| Day 7 | 0/10 | 0/0 | 0/0 | 0/0 | 1/1 | 2/2 | 2/2 |
| Total | 0/10 | 10/10 | 10/10 | 10/10 | 10/10 | 10/10 | 10/10 |

TABLE 3

Effects of LPC on survivabilites (%) in CPA-CLP sepsis mouse mode (SEP008)

| Survivabilities | Controls | | LPC | | | | |
| --- | --- | --- | --- | --- | --- | --- | --- |
| | CPA | CPA + CLP | 1 mpk | 2.5 mpk | 5 mpk | 10 mpk | 20 mpk |
| $1^{st}$ CPA treat | 100 | 100 | 100 | 100 | 100 | 100 | 100 |
| $2^{nd}$ CPA treat | 100 | 100 | 100 | 100 | 100 | 100 | 100 |
| At CLP (day 0) | 100 | 100 | 100 | 100 | 100 | 100 | 100 |
| Day 1 | 100 | 40 | 60 | 80 | 60 | 90 | 90 |
| Day 2 | 100 | 0 | 40 | 60 | 50 | 70 | 80 |
| Day 3 | 100 | 0 | 20 | 30 | 40 | 60 | 60 |
| Day 4 | 100 | 0 | 0 | 10 | 30 | 50 | 40 |
| Day 5 | 100 | 0 | 0 | 0 | 30 | 40 | 20 |
| Day 6 | 100 | 0 | 0 | 0 | 10 | 20 | 20 |
| Day 7 | 100 | 0 | 0 | 0 | 0 | 0 | 0 |
| Total | 100 | 0 | 0 | 0 | 0 | 0 | 0 |

As a result, as can be seen from Tables 2 and 3 above, in the CPA control group, all mice survived during the observational period, 7 days. In the CLP control group, 10 out of 10 animals died within 2 days after CLP, thereby showing 100% mortality. In the LPC 1 mg/kg- and 2.5 mg/kg-dosing groups, all animals died within 4 days and 5 days after CLP, respectively. In the LPC 5 mg/kg-, 10 mg/kg-, 20 mg/kg-dosing groups, all animals died within 7 days after CLP (Table 2). Meanwhile, on day 4 after CLP when all animals of the LPC 1 mg/kg-dosing group died, the LPC 2.5 mg/kg-, 5 mg/kg-, 10 mg/kg-, and 20 mg/kg-dosing groups showed 10%, 30%, 50%, and 40%, respectively (Table 3).

Significant decreases in the body weight were detected just before death in all the CPA-CLP treated groups as compared with the CPA control group. However, no meaningful changes in the body weight were detected in all the LPC dosing groups as compared with the CPA-CLP control group.

As described above, the survival time, which is regarded as the most important index in the sepsis, was significantly increased by all the five doses of LPC in CPA-CLP mice. Accordingly, it can be seen that LPC can increase the survival times of patients with sepsis. Further, the LPC 1 mg/kg-, 2.5 mg/kg-, 5 mg/kg-, and 10 mg/kg-dosing groups showed survival time extension effects in a dose-dependent manner. However, LPC 20 mg/kg-dosing group showed similar or relatively lower effects as compared with the LPC 10 mg/kg-dosing group. Accordingly, in the CPA-CLP model, the minimal effective dose of LPC was determined to be about 1 mg/kg and the optimal effective dose of LPC was observed to be 10 mg/kg.

Example 5

Effects of LPC Isomers on Survivabilities in CPA-CLP-Induced Mouse Model

Figure 2:
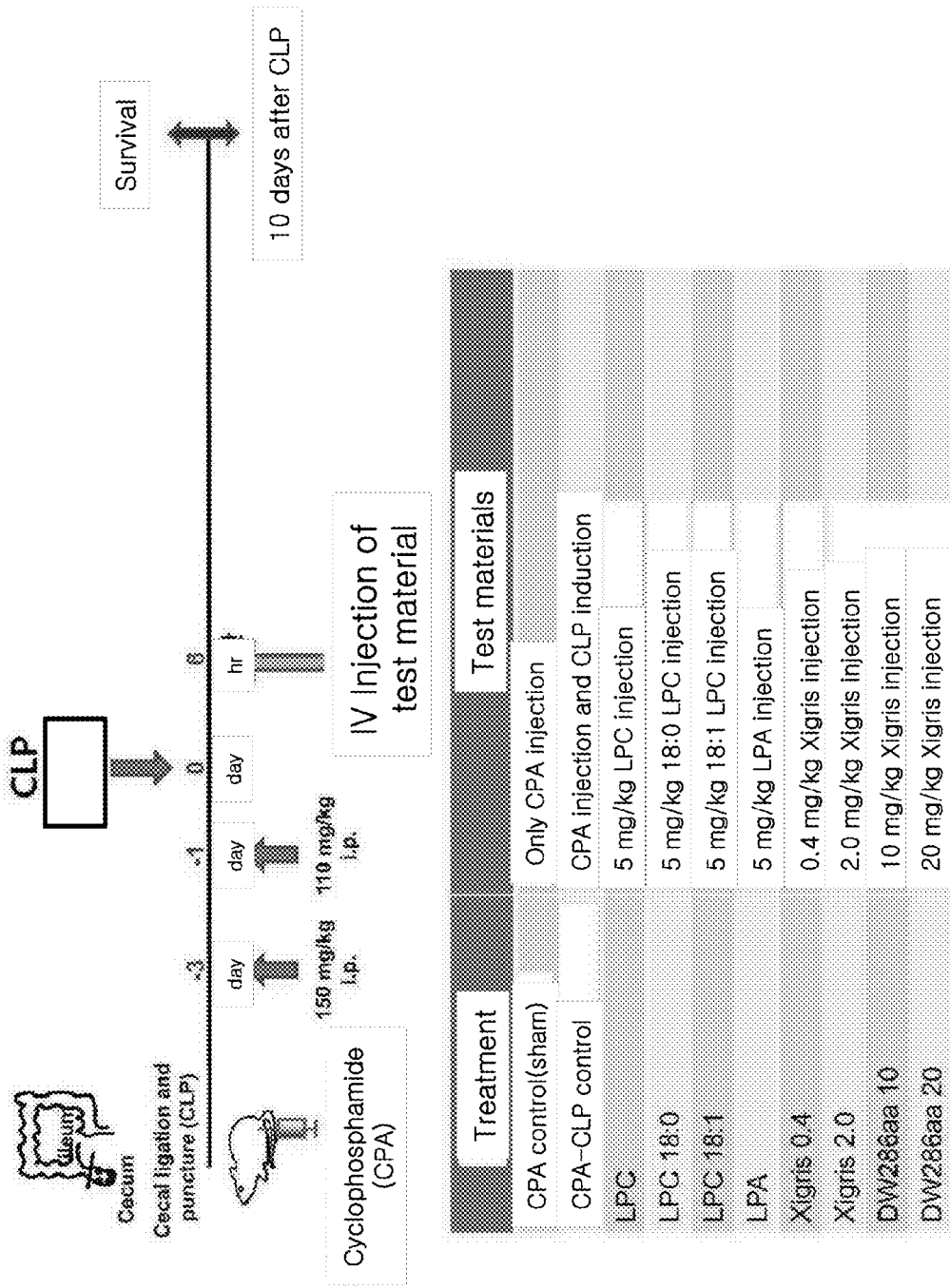
FIG. 2 schematically shows dosing groups and dosing orders of LPC isomers and antibiotics in the CPA-CLP-induced model.

Efficacies of LPC, Xigris, LPA, 18:1 LPC, 18:0 LPC, and DW286AA were compared by using CPA-induced immunosuppressive and then CLP-induced sepsis mice. CPA-CLP sepsis mice were single intravenously dosed with LPC, LPA, 18:1 LPC, and 18:0 LPC (5 mg/kg for each), Xigris (0.4 and 2 mg/kg), and DW286AA (10 and 20 mg/kg), 6 hrs after CLP, respectively. Then, body weight and mortality changes were observed. All test materials were dissolved in sterile physiological saline, and dosed at 10 ml/kg (of body weight) for each. The dosing orders and dosing groups were schematically represented in FIG. 2.

Specifically, ICR mice (6-wk old male, SLC, Japan) were divided into ten groups (ten mice per group), CPA control group (CPA-treated sham CLP operated vehicle dosing group), CPA-CLP control group (CPA-treated CLP operated vehicle dosing group), LPC 5 mg/kg-dosing group after CPA-CLP, Xigris 0.4 mg/kg-dosing group after CPA-CLP, Xigris 2 mg/kg-dosing group after CPA-CLP, LPA 5 mg/kg-dosing group after CPA-CLP, 18:1 LPC 5 mg/kg-dosing group after CPA-CLP, 18:0 LPC 5 mg/kg-dosing group after CPA-CLP, DW286AA 10 mg/kg-dosing group after CPA-CLP, and DW286AA 20 mg/kg-dosing group after CPA-CLP. Test materials were single intravenously dosed at 10 ml/kg (of body weight), 6 hrs after CLP, by using sterile physiological saline as vehicle. That is, CPA-CLP sepsis mice were single intravenously dosed with 5 mg/kg of LPC, LPA, 18:1 LPC, and 18:0 LPC, 0.4 and 2 mg/kg of Xigris, and 10 and 20 mg/kg of DW286AA, 6 hrs after CLP, respectively. All test materials were dissolved in sterile sailine, and dosed at 10 ml/kg (of body weight) for each. In the Sham and CLP control groups, 10 ml/kg of only sterile physiological saline was single intravenously dosed. After dosing, body weight and mortality changes were observed by the procedure as described in Example 3-3.

TABLE 4

Effects of LPC, LPC isomers, Xygris, and DW286aa on mortalities in CPA-CLP sepsis mouse model (SEP009)

| | Controls | | | | | | | | | |
|---|---|---|---|---|---|---|---|---|---|---|
| | | CPA + | LPC | LPC18:0 | LPC18:1 | LPA | Xygris | | DW286aa | |
| Mortalities | CPA | CLP | 5 mpk | 5 mpk | 5 mpk | 5 mpk | 0.4 mpk | 2 mpk | 10 mpk | 20 mpk |
| 1$^{st}$ CPA treat | 0 | 0 | 0 | 0 | 0 | 0 | 0 | 0 | 0 | 0 |
| 2$^{nd}$ CPA treat | 0 | 0 | 0 | 0 | 0 | 0 | 0 | 0 | 0 | 0 |
| At CLP (day 0) | 0 | 0 | 0 | 0 | 0 | 0 | 0 | 0 | 0 | 0 |
| Day 1 | 0 | 4 | 1 | 0 | 0 | 0 | 3 | 0 | 1 | 0 |
| Day 2 | 0 | 6 | 3 | 6 | 10 | 9 | 4 | 5 | 2 | 1 |
| Day 3 | 0 | 0 | 1 | 0 | 0 | 1 | 2 | 1 | 0 | 1 |
| Day 4 | 0 | 0 | 1 | 1 | 0 | 0 | 0 | 3 | 0 | 0 |
| Day 5 | 0 | 0 | 2 | 1 | 0 | 0 | 0 | 0 | 0 | 0 |
| Day 6 | 0 | 0 | 0 | 0 | 0 | 0 | 0 | 0 | 0 | 2 |
| Day 7 | 0 | 0 | 1 | 1 | 0 | 0 | 0 | 0 | 2 | 1 |
| Day 8 | 0 | 0 | 1 | 1 | 0 | 0 | 1 | 1 | 1 | 0 |
| Day 9 | 0 | 0 | 0 | 0 | 0 | 0 | 0 | 0 | 1 | 1 |
| Day 10 | 0 | 0 | 0 | 0 | 0 | 0 | 0 | 0 | 0 | 1 |
| Total | 0 | 10 | 10 | 10 | 10 | 10 | 10 | 10 | 7 | 7 |

TABLE 5

Effects of LPC, LPC isomers, Xygris, and DW286aa on survivabilities (%) in CPA-CLP sepsis mouse model (SEP009)

| | Controls | | | | | | | | | |
|---|---|---|---|---|---|---|---|---|---|---|
| | | CPA + | LPC | LPC18:0 | LPC18:1 | LPA | Xygris | | DW286aa | |
| Mortalities | CPA | CLP | 5 mpk | 5 mpk | 5 mpk | 5 mpk | 0.4 mpk | 2 mpk | 10 mpk | 20 mpk |
| 1$^{st}$ CPA treat | 100 | 100 | 100 | 100 | 100 | 100 | 100 | 100 | 100 | 100 |
| 2$^{nd}$ CPA treat | 100 | 100 | 100 | 100 | 100 | 100 | 100 | 100 | 100 | 100 |
| At CLP (day 0) | 100 | 100 | 100 | 100 | 100 | 100 | 100 | 100 | 100 | 100 |
| Day 1 | 100 | 60 | 90 | 100 | 100 | 100 | 70 | 100 | 90 | 100 |
| Day 2 | 100 | 0 | 60 | 40 | 0 | 90 | 30 | 50 | 70 | 90 |
| Day 3 | 100 | 0 | 50 | 40 | 0 | 0 | 10 | 40 | 70 | 80 |
| Day 4 | 100 | 0 | 40 | 30 | 0 | 0 | 10 | 10 | 70 | 80 |
| Day 5 | 100 | 0 | 20 | 20 | 0 | 0 | 10 | 10 | 70 | 80 |
| Day 6 | 100 | 0 | 20 | 20 | 0 | 0 | 10 | 10 | 70 | 60 |
| Day 7 | 100 | 0 | 10 | 10 | 0 | 0 | 10 | 10 | 50 | 50 |
| Day 8 | 100 | 0 | 0 | 0 | 0 | 0 | 0 | 0 | 40 | 50 |
| Day 9 | 100 | 0 | 0 | 0 | 0 | 0 | 0 | 0 | 30 | 40 |
| Day 10 | 100 | 0 | 0 | 0 | 0 | 0 | 0 | 0 | 30 | 30 |
| Total | 100 | 0 | 0 | 0 | 0 | 0 | 0 | 0 | 30 | 30 |

As a result, as can be seen from Tables 4 and 5 above, all mice of the CPA control group survived during the observational period, 10 days. In the CLP control group, 10 out of 10 animals died within 2 days after CLP, thereby showing 100% mortality. In the LPC 5 mg/kg-dosing group, Xigris 0.4 and 2 mg/kg-dosing groups, and the 18:0 LPC 5 mg/kg-dosing group, all animals died within 8 days after CLP. In LPA 5 mg/kg-dosing group, all animals died within 3 days after CLP (Table 4). Meanwhile, in the 18:1 LPC 5 mg/kg-dosing group, all animals died within 2 days after CLP. In the DW286AA 10 mg/kg- and 20 mg/kg-dosing groups each, three animals (3/10; 30%) survived even 10 days after CLP.

Significant decreases in the body weight were detected just before death in all the CPA-CLP treated groups as compared with the CPA control group. Significant (p<0.01 or p<0.05) increases in the body weight were detected 1 day after CLP in the LPC 5 mg/kg-dosing group and the DW286aa 10 mg/kg- and 20 mg/kg-dosing groups as compared with the CPA-CLP control group, respectively. However, no meaningful changes in the body weight were detected in all the dosing groups as compared with the CPA-CLP control group.

These results support that LPC, Xigris, 18:0 LPC, and DW286AA can increase the survival times of patients with sepsis. Especially, significant increases in survival times and survival rates were detected in the DW286AA 10 mg/kg- and 20 mg/kg-dosing groups. More favorable effects were exhibited in the LPC 5 mg/kg-dosing group as compared with the Xigris 2 mg/kg-dosing group. 18:0 LPC exhibited more favorable effects than 18:1 LPC, and similar effects as compared with equal doses of LPC. This result supports that, besides LPC, LPC isomers can also have effects in enhancement of immunity and treatment of bacterial infections.

Example 6

Figure 3:
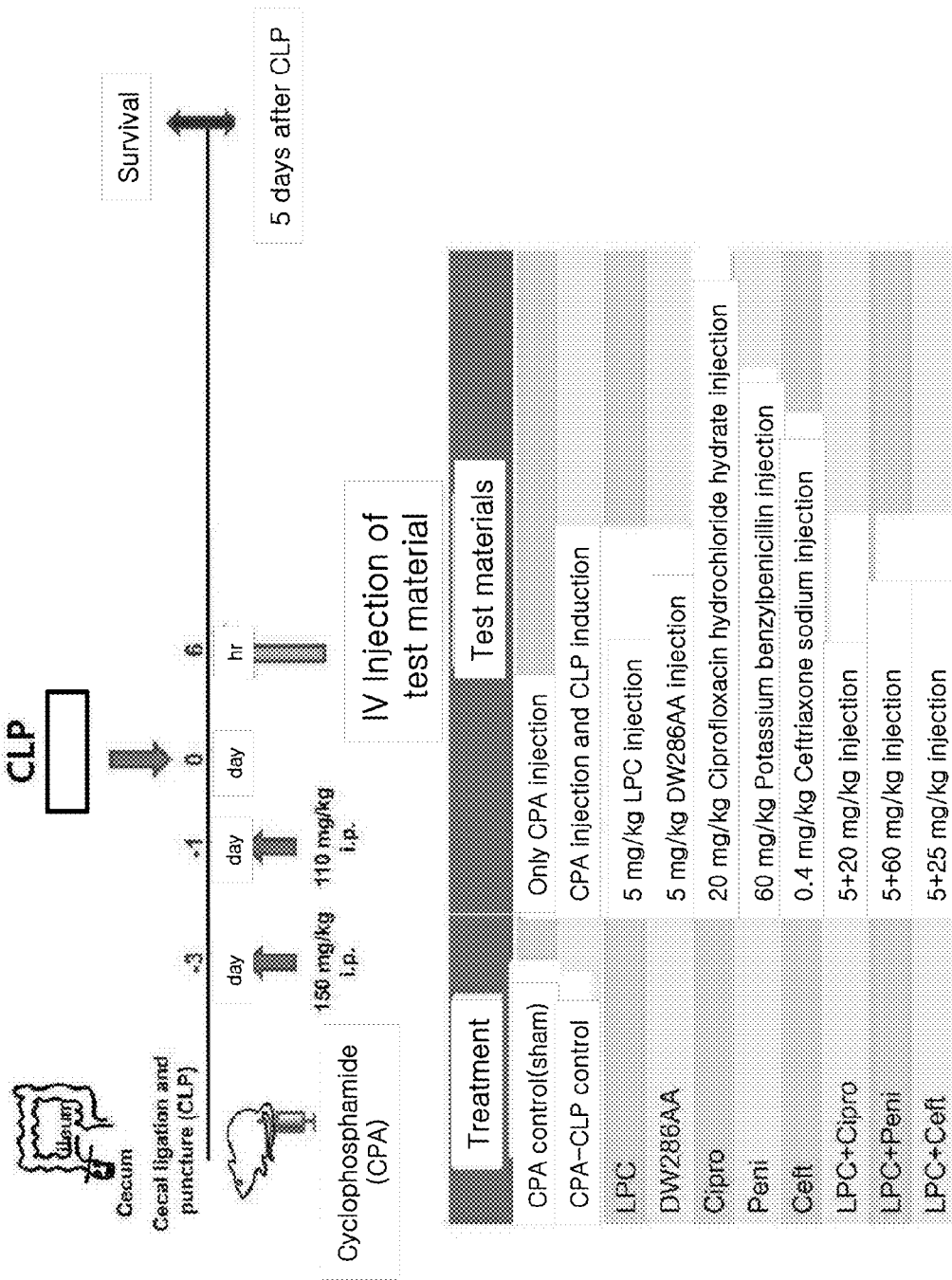
FIG. 3 schematically shows dosing groups and dosing orders of LPC in combination with ciprofloxacin hydrochloride hydrate, potassium benzylpenicillin, and ceftriaxone sodium in the CPA-CLP-induced model.

Effects of LPC and Antibiotics Alone or in Combination on Survivabilities in CPA-CLP-Induced Mouse Model Efficacies of LPC in combination with ciprofloxacin hydrochloride hydrate (Cipro), potassium benzylpenicillin (Peni), and ceftriaxone sodium (Ceft) were compared by using CPA-induced immunosuppressive and then CLP-induced sepsis mice. CPA-CLP sepsis mice were single intravenously dosed with LPC (5 mg/kg), Cipro (20 mg/kg), Peni (60 mg/kg), Ceft (25 mg/kg), LPC+Cipro (5+20 mg/kg), LPC+Peni (5+60 mg/kg), and LPC+Ceft (5+25 mg/kg), 6 hrs after CLP, respectively. Then, body weight and mortality changes were observed. In addition, DW286AA (5 mg/kg) was used as a control agent. All test materials were dissolved in sterile physiological saline and then dosed at 10 ml/kg (of body weight) for each. In all the combination groups, appropriate doses of materials were directly dissolved in an LPC (0.5 mg/ml)-dissolved solution and then dosed, respectively. The dosing order and dosing groups were schematically represented in FIG. 3.

Specifically, ICR mice (6-wk old male, SLC, Japan) were divided into ten groups (ten mice per group), CPA control group (CPA-treated sham CLP operated vehicle dosing group), CPA-CLP control group (CPA-treated CLP operated vehicle dosing group), LPC 5 mg/kg-dosing group after CPA-CLP, DW286AA 5 mg/kg-dosing group after CPA-CLP, Cipro 20 mg/kg-dosing group after CPA-CLP, Pen±60 mg/kg-dosing group after CPA-CLP, Ceft mg/kg-dosing group after CPA-CLP, LPC+Cipro 5+20 mg/kg-dosing group after CPA-CLP, LPC+Peni 5+60 mg/kg-dosing group after CPA-CLP, and LPC+Ceft 5+25 mg/kg-dosing group after CPA-CLP. Test materials were single intravenously dosed at 10 ml/kg (of body weight), 6 hrs after CLP, by using sterile physiological saline as vehicle. That is, CPA-CLP sepsis mice were single intravenously dosed with LPC (5 mg/kg), Cipro (20 mg/kg), Peni (60 mg/kg), Ceft (25 mg/kg), LPC+Cipro (5+20 mg/kg), LPC+Peni (5+60 mg/kg), and LPC+Ceft (5+25 mg/kg), 6 hrs after CLP, respectively. All test materials were dissolved in sterile physiological saline and then dosed at 10 ml/kg (of body weight) for each. In all the composition groups, appropriate doses of materials were directly dissolved in an LPC (0.5 mg/ml)-dissolved solution and then dosed, respectively. After dosing, body weight and mortality changes were observed by the procedure as described in Example 3-3.

TABLE 6

Combination effects of LPC and antibiotics on mortalities in CPA-CLP sepsis mouse model (SEP011)

| Mortalities | Controls | | LPC 5 mpk | DW286aa 5 mpk | Cipro 20 mpk | Peni 60 mpk | Ceft 25 mpk | LPC + Cipro 5 + 20 mpk | LPC + Peni 5 + 60 mpk | LPC + Ceft 5 + 25 mpk |
|---|---|---|---|---|---|---|---|---|---|---|
| | CPA | CPA + CLP | | | | | | | | |
| 1$^{st}$ CPA treat | 0 | 0 | 0 | 0 | 0 | 0 | 0 | 0 | 0 | 0 |
| 2$^{nd}$ CPA treat | 0 | 0 | 0 | 0 | 0 | 0 | 0 | 0 | 0 | 0 |
| At CLP (day 0) | 0 | 0 | 0 | 0 | 0 | 0 | 0 | 0 | 0 | 0 |
| Day 1 | 0 | 6 | 2 | 0 | 0 | 1 | 0 | 0 | 0 | 0 |
| Day 2 | 0 | 4 | 6 | 1 | 6 | 9 | 5 | 3 | 5 | 4 |
| Day 3 | 0 | 0 | 2 | 2 | 4 | 0 | 5 | 4 | 5 | 3 |
| Total | 0 | 10 | 10 | 3 | 10 | 10 | 10 | 7 | 10 | 7 |

TABLE 7

Combination Effects of LPC and antibiotics on survivabilities (%) in CPA-CLP sepsis mouse model (SEP011)

| Survivabilities | Controls | | LPC 5 mpk | DW286aa 5 mpk | Cipro 20 mpk | Peni 60 mpk | Ceft 25 mpk | LPC + Cipro 5 + 20 mpk | LPC + Peni 5 + 60 mpk | LPC + Ceft 5 + 25 mpk |
|---|---|---|---|---|---|---|---|---|---|---|
| | CPA | CPA + CLP | | | | | | | | |
| 1$^{st}$ CPA treat | 100 | 100 | 100 | 100 | 100 | 100 | 100 | 100 | 100 | 100 |
| 2$^{nd}$ CPA treat | 100 | 100 | 100 | 100 | 100 | 100 | 100 | 100 | 100 | 100 |
| At CLP (day 0) | 100 | 100 | 100 | 100 | 100 | 100 | 100 | 100 | 100 | 100 |
| Day 1 | 100 | 40 | 80 | 100 | 100 | 90 | 100 | 100 | 100 | 100 |
| Day 2 | 100 | 0 | 20 | 90 | 40 | 0 | 50 | 70 | 50 | 60 |
| Day 3 | 100 | 0 | 0 | 70 | 0 | 0 | 0 | 30 | 0 | 30 |
| Total | 100 | 0 | 0 | 70 | 0 | 0 | 0 | 30 | 0 | 30 |

As a result, as can be seen from Tables 6 and 7 above, all mice of the CPA control group survived during the observational period, 3 days. However, in the CLP control and Peni dosing groups, 10 out of 10 animals died within 2 days after CLP, thereby showing 100% mortality. In the LPC, Cipro, Ceft, and LPC+Peni dosing groups, all animals died within 3 days after CLP. However, the survival rates were decreased or the times of death were delayed in LPC and antibiotic combinations, that is, the LPC+Cipro, LPC+Peni, and LPC+Ceft dosing groups, as compared with LPC alone or antibiotics alone (Table 6). Meanwhile, in the LPC+Ceft and DW286aa dosing groups, three animals (3/10; 30%) and seven animals (7/10; 70%) survived even 3 days after CLP, respectively (Table 7).

Significant decreases in the body weight were detected from 1 day after CLP in all the CPA-CLP treated groups as compared with the CPA control group. Significant ($p<0.05$) decreases in the body weight were detected 1 day after CLP in the LPC dosing group as compared with the CPA-CLP control group. However, no meaningful changes in the body weight were detected in all the dosing groups as compared with the CPA-CLP control group.

The increases in the survival rate were detected in the LPC+Cipro, LPC+Peni, and LPC+Ceft dosing groups as compared with the LPC alone group and each of the antibiotic alone groups. This result means that their effects were increased by combinations of LPC and antibiotics, and thus supports that the combinational agents of the present invention can have superior effects in enhancement of immunity and treatment of bacterial infections.

Example 7

Figure 4:
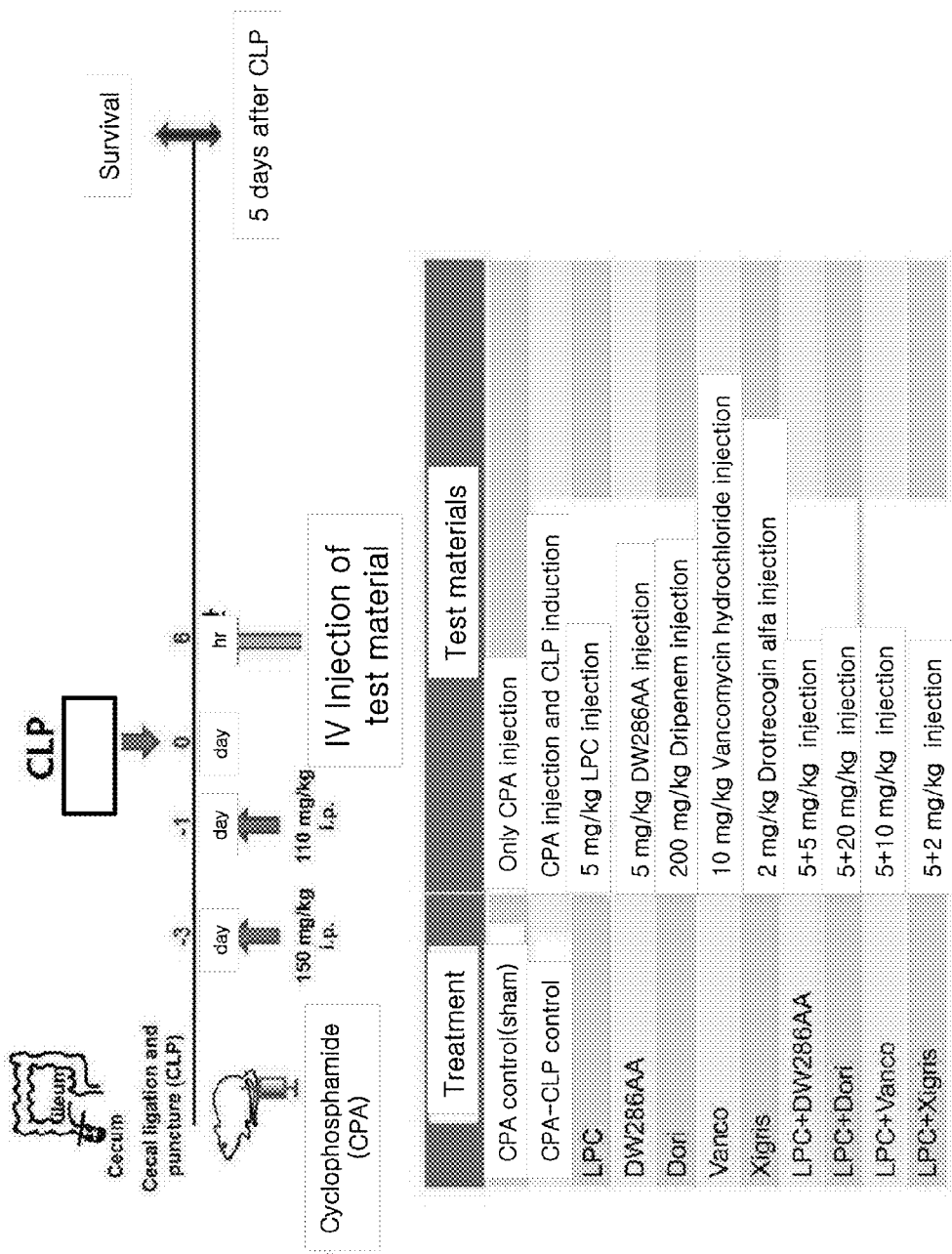
FIG. 4 schematically shows dosing groups and dosing orders of LPC in combination with doripenem, vancomycin hydrochloride, and drotrecogin alfa (activated) in the CPA-CLP-induced model.

Effects of LPC and Antibiotics Alone or in Combination on Survivabilities in CPA-CLP-Induced Mouse Model Efficacies of LPC in combination with doripenem (Dori), vancomycin hydrochloride (Vanco), and drotrecogin alfa (activated) (Xigris) were compared by using CPA-induced immunosuppressive and then CLP-induced sepsis mice. CPA-CLP sepsis mice were single intravenously dosed with LPC (5 mg/kg), DW286AA (5 mg/kg), Dori (200 mg/kg), Vanco (10 mg/kg), Xigris (2 mg/kg), LPC+DW286AA (5+5 mg/kg), LPC+Dori (5+200 mg/kg), LPC+Vanco (5+10 mg/kg), and LPC+Xigris (5+2 mg/kg), 6 hrs after CLP, respectively. Then, body weight and mortality changes were observed. All test materials were dissolved in sterile physiological saline and then dosed at 10 ml/kg (of body weight) for each. In all the composition groups, appropriate doses of materials were directly dissolved in an LPC (0.5 mg/ml)-dissolved solution and then dosed, respectively. The dosing orders and dosing groups were schematically represented in FIG. 4.

Specifically, ICR mice (6-wk old male, SLC, Japan) were divided into 11 groups (ten mice per group), CPA control group (CPA-treated sham CLP operated vehicle dosing group), CPA-CLP control group (CPA-treated CLP operated vehicle dosing group), LPC 5 mg/kg-dosing group after CPA-CLP, DW286AA 5 mg/kg-dosing group after CPA-CLP, Dor±200 mg/kg-dosing group after CPA-CLP, Vanco 10 mg/kg-dosing group after CPA-CLP, Xigris 2 mg/kg-dosing group after CPA-CLP, LPC+DW286AA 5+5 mg/kg-dosing group after CPA-CLP, LPC+Dori 5+200 mg/kg-dosing group after CPA-CLP, LPC+Vanco 5+10 mg/kg-dosing group after CPA-CLP, and LPC+Xigris 5+2 mg/kg-dosing group after CPA-CLP. Test materials were single intravenously dosed at 10 ml/kg (of body weight), 6 hrs after CLP, respectively, by using sterile physiological saline as vehicle. That is, CPA-CLP sepsis mice were single intravenously dosed with LPC (5 mg/kg), DW286AA (5 mg/kg), Dori (200 mg/kg), Vanco (10 mg/kg), Xigris (2 mg/kg), LPC+DW286AA (5+5 mg/kg), LPC+Dori (5+200 mg/kg), LPC+Vanco (5+10 mg/kg), and LPC+Xigris (5+2 mg/kg), 6 hrs after CLP, respectively. All test materials were dissolved in sterile physiological saline and then dosed at 10 ml/kg (of body weight) for each. In all composition groups, appropriate doses of materials were directly dissolved in an LPC (0.5 mg/ml)-dissolved solution and then dosed, respectively. After dosing, body weight and mortality changes were observed by the procedure as described in Example 3-3.

TABLE 8

Combination effects of LPC and antibiotics on mortalities in CPA-CLP sepsis mouse model (SEP012)

| Mortalities | Controls | | LPC 5 mpk | DW286aa 5 mpk | Dori 200 mpk | Vanco 10 mpk | Xigris 25 mpk | LPC + 286aa 5 + 5 mpk | LPC + Dori 5 + 200 mpk | LPC + Vanco 5 + 10 mpk | LPC + Xigris 5 + 2 mpk |
| --- | --- | --- | --- | --- | --- | --- | --- | --- | --- | --- | --- |
| | CPA | CPA + CLP | | | | | | | | | |
| 1$^{st}$ CPA treat | 0 | 0 | 0 | 0 | 0 | 0 | 0 | 0 | 0 | 0 | 0 |
| 2$^{nd}$ CPA treat | 0 | 0 | 0 | 0 | 0 | 0 | 0 | 0 | 0 | 0 | 0 |
| At CLP (day 0) | 0 | 0 | 0 | 0 | 0 | 0 | 0 | 0 | 0 | 0 | 0 |
| Day 1 | 0 | 5 | 1 | 0 | 0 | 0 | 0 | 0 | 0 | 0 | 0 |
| Day 2 | 0 | 5 | 6 | 3 | 5 | 7 | 7 | 0 | 3 | 4 | 3 |
| Day 3 | 0 | 0 | 2 | 3 | 3 | 3 | 2 | 1 | 2 | 2 | 4 |
| Total | 0 | 10 | 9 | 6 | 8 | 10 | 9 | 1 | 5 | 6 | 7 |

TABLE 9

Combination Effects of LPC and antibiotics on
survivabilities (%) in CPA-CLP sepsis mouse model (SEP012)

| Survivalities | Controls | | | | | | | | | | |
| --- | --- | --- | --- | --- | --- | --- | --- | --- | --- | --- | --- |
| | CPA | CPA + CLP | LPC 5 mpk | DW286aa 5 mpk | Dori 200 mpk | Vanco 10 mpk | Xigris 25 mpk | LPC + 286aa 5 + 5 mpk | LPC + Dori 5 + 200 mpk | LPC + Vanco 5 + 10 mpk | LPC + Xigris 5 + 2 mpk |
| $1^{st}$ CPA treat | 100 | 100 | 100 | 100 | 100 | 100 | 100 | 100 | 100 | 100 | 100 |
| $2^{nd}$ CPA treat | 100 | 100 | 100 | 100 | 100 | 100 | 100 | 100 | 100 | 100 | 100 |
| At CLP (day 0) | 100 | 100 | 100 | 100 | 100 | 100 | 100 | 100 | 100 | 100 | 100 |
| Day 1 | 100 | 50 | 90 | 100 | 100 | 100 | 100 | 100 | 100 | 100 | 100 |
| Day 2 | 100 | 0 | 30 | 70 | 50 | 30 | 30 | 100 | 70 | 60 | 70 |
| Day 3 | 100 | 0 | 10 | 40 | 20 | 0 | 10 | 90 | 50 | 40 | 30 |
| Total | 100 | 0 | 10 | 40 | 20 | 0 | 10 | 90 | 50 | 40 | 30 |

As a result, as can be seen from Tables 8 and 9 above, all mice of the CPA control group survived during the observational period, 3 days. However, in the CLP control group, 10 out of 10 animals died within 2 days after CLP, thereby showing 100% mortality. In the Vanco dosing group, all animals died within 3 days after CLP. In the LPC, Dori, and Xigris dosing groups, 9, 8, and 10 animals died within 3 days after CLP, respectively. However, the survival rates were decreased or the times of death were delayed in LPC and antibiotic combinations, that is, the LPC+Dori, LPC+Vanco, and LPC+Xigris dosing groups, as compared with LPC alone or DW286AA, Dori, Vanco, and Xigris alone (Table 8). Meanwhile, in the DW286AA, LPC+DW286AA, LPC+Dori, LPC+Vanco, and LPC+Xigris dosing groups, four animals (4/10; 40%), nine animals (9/10; 90%), five animals (5/10; 50%), four animals (4/10; 40%), and three animals (3/10; 30%) survived even 3 days after CLP, respectively (Table 9).

Significant decreases in the body weight were detected from 1 day after CLP in all the CPA-CLP treated groups as compared with the CPA control group. However, no meaningful changes in the body weight were detected in all the dosing groups as compared with the CPA-CLP control group.

The increases in the survival rate were detected in the LPC+DW286AA, LPC+Dori, LPC+Vanco, and LPC+Xigris dosing groups as compared with the LPC alone group and each of the antibiotic alone groups. This result means that their effects were increased by combinations of LPC and antibiotics, and thus supports that the combinational agents of the present invention can have superior effects in enhancement of immunity and treatment of bacterial infections.

Example 8

Figure 5:
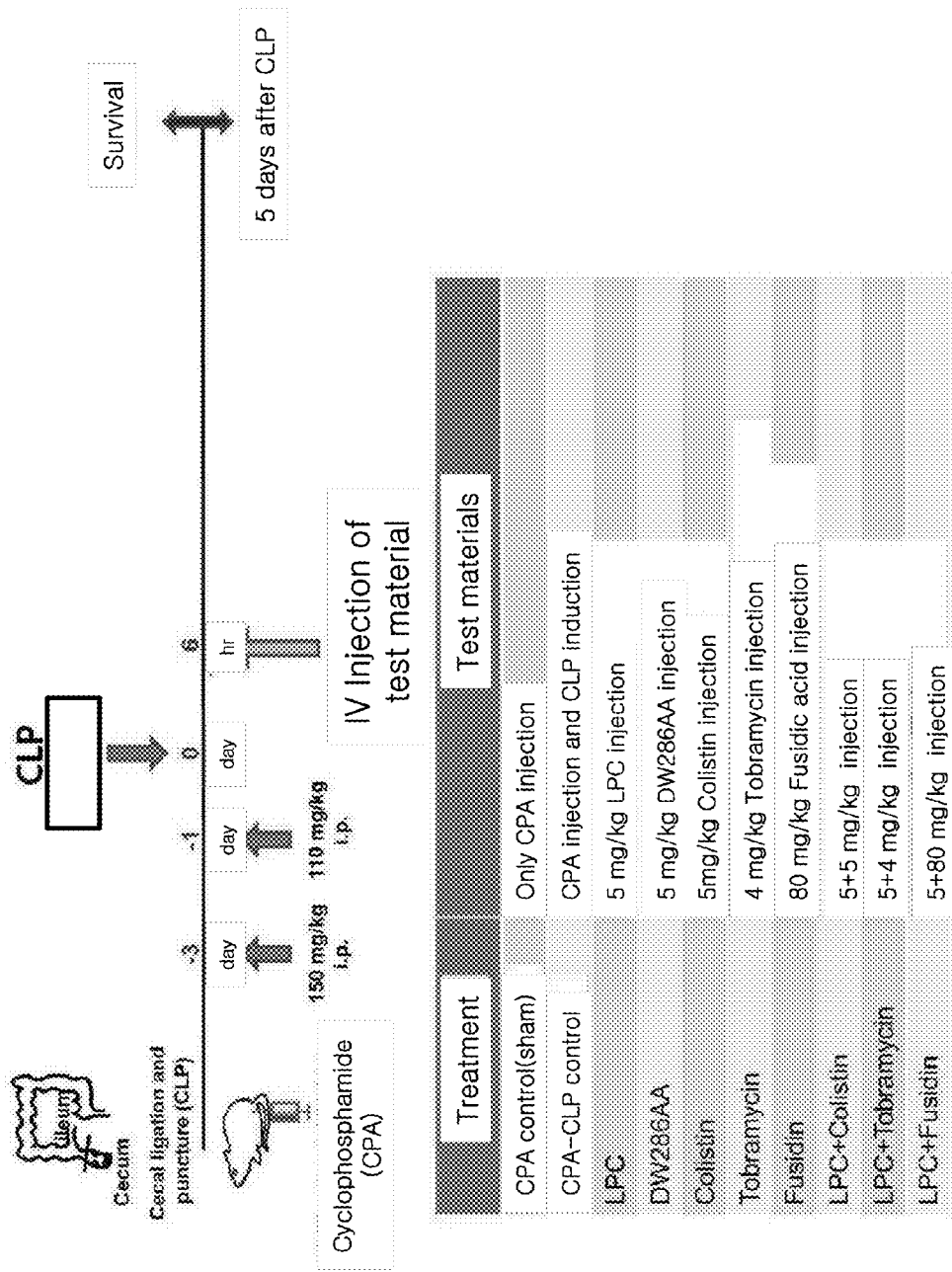
FIG. 5 schematically shows dosing groups and dosing orders of LPC in combination with colistin, tobramycin, and fusidic acid in the CPA-CLP-induced model.

Effects of LPC and Antibiotics Alone or in Combination on Survivabilities in CPA-CLP-Induced Mouse Model Efficacies of LPC in combination with Colistin, tobramycin (Tobra), and fusidic acid sodium (Fusidin) were compared by using CPA-induced immunosuppressive and then CLP-induced sepsis mice. CPA-CLP sepsis mice were single intravenously dosed with LPC (5 mg/kg), LPC (5 mg/kg), colistin (5 mg/kg), tobramycin (4 mg/kg), fusidin (80 mg/kg), LPC+colistin (5+5 mg/kg), LPC+tobramycin (5+4 mg/kg), and LPC+fusidin (5+80 mg/kg), respectively, 6 hrs after CLP, respectively. Then, body weight and mortality changes were observed. In addition, DW286AA (5 mg/kg) was used as a control agent. All test materials were dissolved in sterile physiological saline and then dosed at 10 ml/kg (of body weight) for each. In all the combination groups, appropriate doses of materials were directly dissolved in an LPC (0.5 mg/ml)-dissolved solution and then dosed, respectively. The dosing orders and dosing groups were schematically represented in FIG. 5.

Specifically, ICR mice (6-wk old male, SLC, Japan) were divided into 10 groups, CPA control group (CPA-treated sham CLP operated vehicle dosing group), DW286AA 5 mg/kg-dosing group after CPA-CLP, LPC 5 mg/kg-dosing group after CPA-CLP, colistin 5 mg/kg-dosing group after CPA-CLP, tobramycin 4 mg/kg-dosing group after CPA-CLP, fusidin 80 mg/kg-dosing group after CPA-CLP, LPC+colistin 5+5 mg/kg-dosing group after CPA-CLP, LPC+tobramycin 5+4 mg/kg-dosing group after CPA-CLP, and LPC+fusidin 5+80 mg/kg-dosing group after CPA-CLP. Test materials were single intravenously dosed at 10 ml/kg (of body weight), 6 hrs after CLP, respectively, by using sterile physiological saline as vehicle. That is, CPA-CLP sepsis mice were single intravenously dosed with LPC (5 mg/kg), DW286AA (5 mg/kg), colistin (5 mg/kg), tobramycin (4 mg/kg), fusdin (80 mg/kg), LPC+colistin (5+5 mg/kg), LPC+tobramycin (5+4 mg/kg), and LPC+fusidin (5+80 mg/kg), 6 hrs after CLP, respectively. All test materials were dissolved in sterile physiological saline and then dosed at 10 ml/kg (of body weight) for each. In all the composition groups, appropriate doses of materials were directly dissolved in an LPC (0.5 mg/ml)-dissolved solution and then dosed, respectively. After dosing, body weight and mortality changes were observed by the procedure as described in Example 3-3.

TABLE 10

Combination effects of LPC and antibiotics on
mortalities in CPA-CLP sepsis mouse model (SEP013)

| Mortalities | Controls | | | | | | | LPC + Colistin 5 + 5 mpk | LPC + Tobra 5 + 4 mpk | LPC + Fusidin 5 + 80 mpk |
| --- | --- | --- | --- | --- | --- | --- | --- | --- | --- | --- |
| | CPA | CPA + CLP | LPC 5 mpk | DW286aa 5 mpk | Colistin 5 mpk | Tobra 4 mpk | Fusidin 80 mpk | | | |
| 1st CPA treat | 0 | 0 | 0 | 0 | 0 | 0 | 0 | 0 | 0 | 0 |
| 2nd CPA treat | 0 | 0 | 0 | 0 | 0 | 0 | 0 | 0 | 0 | 0 |
| At CLP (day 0) | 0 | 0 | 0 | 0 | 0 | 0 | 0 | 0 | 0 | 0 |
| Day 1 | 0 | 4 | 2 | 0 | 1 | 2 | 2 | 0 | 1 | 1 |
| Day 2 | 0 | 6 | 5 | 0 | 5 | 5 | 5 | 5 | 3 | 4 |
| Day 3 | 0 | 0 | 2 | 2 | 2 | 1 | 1 | 1 | 1 | 0 |
| Total | 0 | 10 | 9 | 2 | 9 | 8 | 8 | 6 | 5 | 5 |

TABLE 11

Combination effects of LPC and antibiotics on
survivabilities (%) in CPA-CLP sepsis mouse model (SEP013)

| Survivalities | Controls | | | | | | | LPC + Colistin 5 + 5 mpk | LPC + Tobra 5 + 4 mpk | LPC + Fusidin 5 + 80 mpk |
| --- | --- | --- | --- | --- | --- | --- | --- | --- | --- | --- |
| | CPA | CPA + CLP | LPC 5 mpk | DW286aa 5 mpk | Colistin 5 mpk | Tobra 4 mpk | Fusidin 80 mpk | | | |
| 1st CPA treat | 100 | 100 | 100 | 100 | 100 | 100 | 100 | 100 | 100 | 100 |
| 2nd CPA treat | 100 | 100 | 100 | 100 | 100 | 100 | 100 | 100 | 100 | 100 |
| At CLP (day 0) | 100 | 100 | 100 | 100 | 100 | 100 | 100 | 100 | 100 | 100 |
| Day 1 | 100 | 60 | 80 | 100 | 90 | 80 | 80 | 100 | 90 | 90 |
| Day 2 | 100 | 0 | 30 | 100 | 40 | 30 | 30 | 50 | 60 | 50 |
| Day 3 | 100 | 0 | 10 | 80 | 20 | 20 | 20 | 40 | 50 | 50 |
| Total | 100 | 0 | 10 | 80 | 20 | 20 | 20 | 40 | 50 | 50 |

As a result, as can be seen from Tables 10 and 11 above, all mice of the CPA control group survived during the observational period, 3 days. However, in the CLP control group, 10 out of 10 animals died within 2 days after CLP, thereby showing 100% mortality. In the groups of LPC, Fusidin, colistin, and tobramycin alone, 9, 8, 9, and 8 animals died within 3 days after CLP, respectively. However, the survival rates were decreased or the times of death were delayed in the groups of LPC in combination with colistin, tobramycin, and fusidin (Table 10). Meanwhile, in the DW286AA, LPC+colistin, LPC+tobramycin, and LPC+fusidin dosing groups, eight animals (8/10; 80%), four animals (4/10; 40%), five animals (5/10; 50%), and five animals (5/10; 50%) survived even 3 days after CLP, respectively (Table 11). Significant decreases in the body weight were detected from 1 day after CLP in all the CPA-CLP treated groups as compared with the CPA control group. However, no meaningful changes in the body weight were detected in all the dosing groups as compared with the CPA-CLP control group.

The increases in the survival rate and survival period were detected in the LPC+colistin, LPC+tobramycin, and LPC+fusidin dosing groups as compared with the LPC alone group and each of the antibiotic alone groups. This result means that their effects were increased by combinations of LPC and antibiotics, and thus supports that the combinational agents of the present invention can have superior effects in enhancement of immunity and treatment of bacterial infections.

Example 9

Effects of LPC in Combination with Novel Quinoline Based Antibiotic DW286AA on Survivability To find suitable dosing regime of LPC and DW286AA combination during the development of new therapeutic agents against sepsis, evaluation was conducted by using CPA-CLP— and CPA-induced immunosuppressive mice. CPA-CLP mice and CPA-induced immunosuppressive mice were dosed with LPC and DW286AA alone, Mix (LPC:DW286AA 2:1), LPC-pre-treated (2 times) and then DW286AA treated (2 times), and DW286AA-pre-treated and LPC treated. Then, mortalities, changes in thymus and spleen weights, changes in white blood cell (WBC) number, and changes in thymic and splenic CD3+, CD4+, CD8+, and TNF-α+ cell numbers, were evaluated together with changes in bone marrow polychromatic erythrocytes contain micronuclei (MNPCE) number.

Figure 6:
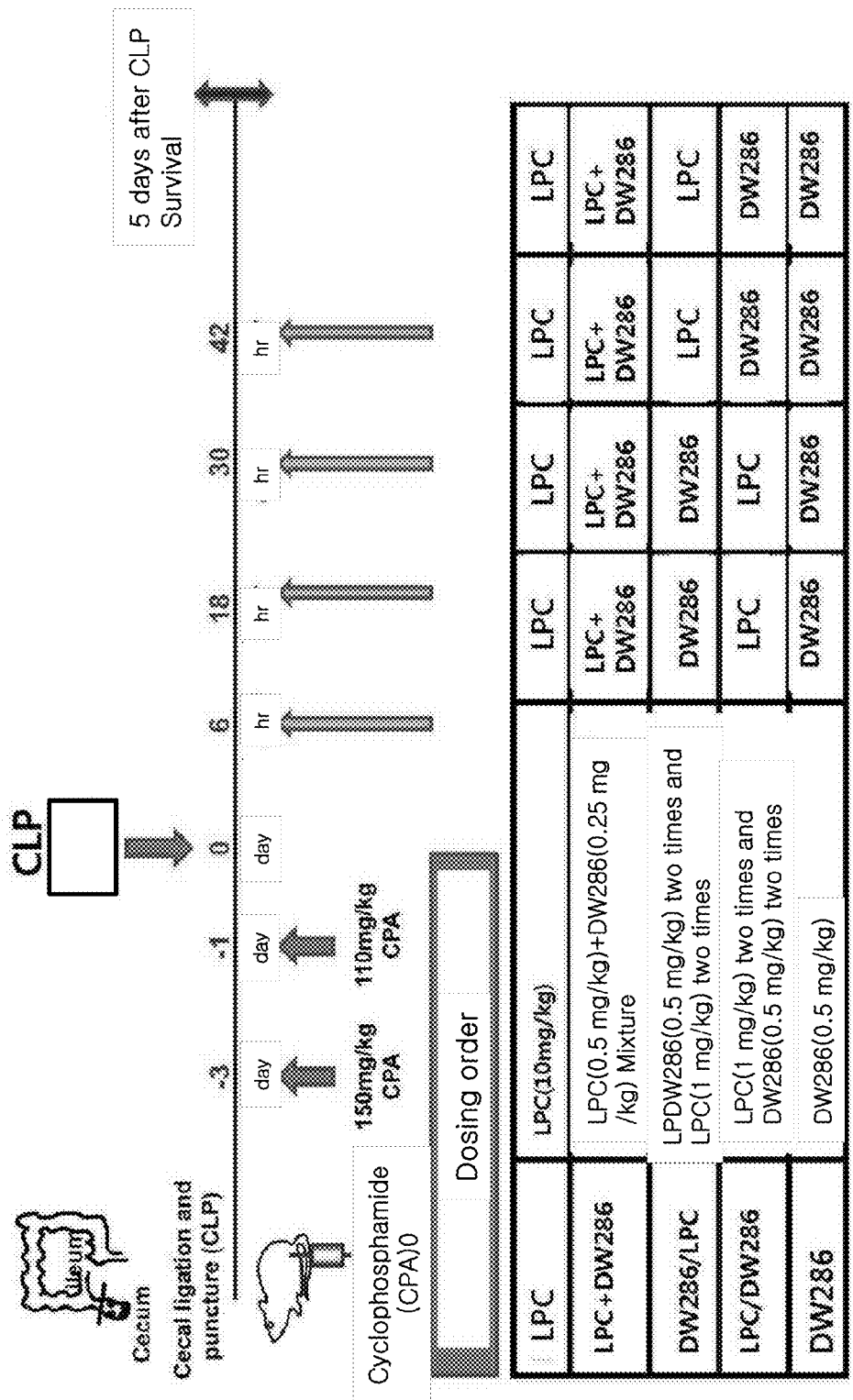
FIG. 6 schematically shows dosing groups and dosing orders of LPC and DW286AA in the CPA-CLP-induced model and CPA-induced immunosuppressive mode.

The mice were divided into eight or nine (including a vehicle control group) groups with 9 mice per group, INTACT control: normal vehicle control group (vehicle: 5% human serum albumin), CPA control: CPA-induced immunosuppressive vehicle control group, CPA-CLP control: CPA and CLP treated vehicle control group, LPC: LPC 1 mg/kg-dosing group, Mix: LPC-DW286AA (2:1) combination 0.75 mg/kg-dosing group, DW286-LPC: DW286 0.5 mg/kg-pre-dosing (2 times) and then LPC 1 mg/kg-dosing (2 times), LPC-DW286: LPC 1 mg/kg pre-dosing (2 times) and then DW286AA 0.5 mg/kg (2 times)-dosing group, and DW286: DW286AA 0.5 mg/kg-dosing group. The dosing orders and dosing groups were schematically represented in FIG. 6. Appropriate doses of candidate materials were dissolved in 5% human serum albumin, and subcutaneously dosed at 10 ml/kg (of body weight), 4 times 12-hr intervals from 6 hrs after CLP or 24 hrs after last CPA-dosing, respectively. In the INTACT, CPA, or CPA-CLP control groups, an equal volume of 5% human serum albumin was dosed by the same procedure.

9-1. Changes on the mortality and body weights of CPA-CLP Model

Any mortality was recorded in CPA and Intact controls, but all animals (9/9; 100%) were died within 2 days after CLP in CPA-CLP control, 6 and 3 animals were died at 1 and 2 days after CLP, respectively. However, all animals in LPC, LPC-DW286 and DW286 groups were died within 4 days after CLP, and with 5 days after CLP in Mix and DW286-LPC groups. Higher early survival rates were detected in DW286-LPC group than that of Mix (table 12).

From 1 day after CLP, significantly ($p<0.01$ or $p<0.05$) decreases on the body weight were detected in CPA and CLP treated groups compared to that of intact control, respectively. No meaningful changes on the body weight were detected in all tested groups compared to that of CPA or CPA-CLP controls in the present study (table 12). The body weight gains in the CPA control group were showed −3.95% changes as compared with the INTACT control group. The body weights were changed in LPC, Mix, DW286-LPC, LPC-DW286, and DW286 dosing groups as −12.35, −17.65, 2.16, −8.82, and −1.37% as compared to the CPA control group, respectively.

It was determined that the decreases in the body weight in all the CPA dosing groups result from direct toxicity of CPA, and it was observed that LPC and DW286 did not inhibit the decreases in the body weight induced by CPA dosing.

Meanwhile, slight decreases in the body weight after dosing of test materials were considered as a secondary effect of irritation or the like due to subcutaneous injection, Further, it was observed that mortalities due to CPA-CLP were significantly reduced by dosing of LPC and DW286AA alone. More favorable survival rates were shown in the Mix group and the DW286-LPC group (DW286AA pre-dosing and then LPC dosing) as compared with the LPC alone group and the DW286AA alone group, and especially, higher early survival rates were detected in the DW286-LPC group than the Mix group (Table 13). It can be anticipated that the DW286AA pre-dosing and then LPC dosing regime is more suitable for treating sepsis.

TABLE 12

Changes of body weight and mortalities detected in CPA-CLP mice

| Body weight | At First CPA dosing[1] | At CLP[1] | Days after CLP | | | | | Gains[2] |
|---|---|---|---|---|---|---|---|---|
| | | | 1 day | 2 days | 3 days | 4 days | 5 days | |
| Controls | | | | | | | | |
| Intact | 34.32 ± 1.32 | 33.90 ± 1.42 | 36.10 ± 1.86 | 37.14 ± 2.16 | 38.09 ± 2.28 | 37.44 ± 1.59 | 39.57 ± 2.14 | 5.67 ± 2.13 |
| CPA | 34.50 ± 1.19 | 33.61 ± 1.45 | 31.49 ± 1.67* | 30.58 ± 1.95* | 31.27 ± 1.76* | 32.71 ± 1.53* | 33.86 ± 1.73* | 0.24 ± 1.88 |
| CPA-CLP | 34.66 ± 1.01 | 33.73 ± 1.39 | 30.87 ± 1.89** | ND[3] | ND | ND | ND | ND |
| Test groups | | | | | | | | |
| LPC | 34.53 ± 1.24 | 32.98 ± 1.65 | 30.10 ± 1.23* | 29.47 ± 1.46** | 31.40 ± 0.28** | ND | ND | ND |
| Mix | 34.20 ± 1.36 | 33.17 ± 1.35 | 30.44 ± 1.68* | 31.27 ± 2.04** | 31.20 ± 2.86** | 31.17 ± 2.11** | ND | ND |
| DW286-LPC | 34.10 ± 1.35 | 33.21 ± 1.40 | 29.99 ± 1.73* | 29.82 ± 1.14* | 30.15 ± 2.24* | 30.67 ± 1.43** | ND | ND |
| LPC-DW286 | 34.48 ± 1.16 | 33.44 ± 1.28 | 31.22 ± 1.18* | 31.30 ± 1.18** | 30.73 ± 1.79** | ND | ND | ND |
| DW286 | 34.32 ± 1.32 | 33.77 ± 1.42 | 31.50 ± 1.34* | 29.88 ± 0.98* | 30.97 ± 0.99** | ND | ND | ND | n = 9;
(Mean ± S.D.), g;
[1]Overnight fasted;
[2]Body weight gains during 5 days after CLP,
[3]Not detected because all animals were died;
*$p < 0.01$ and **$p < 0.05$ compared to that of intact control by MW test.

| | Controls | | | Test groups | | | | |
|---|---|---|---|---|---|---|---|---|
| Mortalities | Intact | CPA | CPA-CLP | LPC | Mix | DW286-LPC | LPC-DW286 | DW286 |
| At CLP | 0.9 (100%)[1] | 0.9 (100%) | 0.9 (100%) | 0.9 (100%) | 0.9 (100%) | 0.9 (100%) | 0.9 (100%) | 0.9 (100%) |
| 1 day after CLP | 0.9 (100%) | 0.9 (100%) | 6.9 (33.33%) | 4.9 (55.55%) | 2.9 (77.77%) | 0.9 (100%) | 4.9 (55.55%) | 0.9 (100%) |
| 2 days after CLP | 0.9 (100%) | 0.9 (100%) | 3.3 (0%) | 2.5 (33.33%) | 4.7 (33.33%) | 4.9 (55.55%) | 2.5 (33.33%) | 5.9 (44.44%) |
| 3 days after CLP | 0.9 (100%) | 0.9 (100%) | 0.0 (0%) | 1.3 (22.22%) | 0.3 (33.33%) | 1.5 (44.44%) | 0.3 (33.33%) | 1.4 (33.33%) |
| 4 days after CLP | 0.9 (100%) | 0.9 (100%) | 0.0 (0%) | 2.2 (0%) | 0.3 (33.33%) | 1.4 (33.33%) | 3.3 (0%) | 3.3 (0%) |
| 5 days after CLP | 0.9 (100%) | 0.9 (100%) | 0.0 (0%) | 0.0 (0%) | 3.3 (0%) | 3.3 (0%) | 0.0 (0%) | 0.0 (0%) |
| Total | 0.9 (100%) | 0.9 (100%) | 9.9 (0%) | 9.9 (0%) | 9.9 (100%) | 9.9 (100%) | 9.9 (100%) | 9.9 (100%) |

[1]Number of died animals total numbers of observed animal (Survival rate)

TABLE 13

| Group | Dose mg/kg | Dosing Day 0 | 1 | 2 | Days after dosing 3 | 4 |
|---|---|---|---|---|---|---|
| Sham | | 100 (9/9) | 100 (9/9) | 100 (9/9) | 100 (9/9) | 100 (9/9) |
| CPA | | 100 (9/9) | 100 (9/9) | 100 (9/9) | 100 (9/9) | 100 (9/9) |
| CPA + CLP | | 100 (9/9) | 33.3 (3/9) | 0 (0/9) | | |
| LPC | 1 | 100 (9/9) | 56 (5/9) | 33 (3/9) | 22 (2/9) | 0 (0/9) |
| LPC + DW286 | LPC(0.5) + DW286(0.25) | 100 (9/9) | 78 (7/9) | 33 (3/9) | 33 (3/9) | 33 (3/9) |
| DW286/LPC | DW286(0.5)/ LPC(1.0) | 100 (9/9) | 100 (9/9) | 56 (5/9) | 44 (4/9) | 33 (3/9) |
| LPC/DW286 | LPC(1.0)/DW286 (0.5) | 100 (9/9) | 56 (5/9) | 33.3 (3/9) | 33 (3/9) | 0 (0/9) |
| DW286 | 0.5 | 100 (9/9) | 100 (9/9) | 44 (4/9) | 33 (3/9) | 0 (0/9) |

9-2. Changes on the Body Weights of CPA-Treated Model

Significantly ($p<0.01$) decreases on the body weight were detected in all CPA treated groups compared to that of intact control, respectively. No meaningful changes on the body weight were detected in all tested groups compared to that of CPA controls in the present study. In addition quite similar body weight gains after initial dosing to sacrifice were also detected in all tested groups including CPA control (Table 14)

TABLE 14

Changes of body weight detected in CPA-treated mice

| Body weight | At First CPA dosing [1] | At Dosing [1] | Days after second CPA-dosing 1 day | 2 days | Gains [2] |
|---|---|---|---|---|---|
| Controls | | | | | |
| Intact | 36.34 ± 0.81 | 35.33 ± 1.86 | 40.26 ± 1.04 | 41.23 ± 1.53 | 5.90 ± 0.76 |
| CPA | 36.80 ± 1.73 | 32.78 ± 1.18* | 37.78 ± 2.03* | 38.44 ± 2.04* | 5.67 ± 1.66 |
| Test groups | | | | | |
| LPC | 36.58 ± 1.36 | 32.08 ± 1.47* | 36.54 ± 1.72* | 37.04 ± 1.47* | 4.97 ± 1.67 |
| Mix | 36.41 ± 1.82 | 32.66 ± 1.70* | 36.00 ± 1.72* | 37.32 ± 1.67* | 4.67 ± 1.07 |
| DW286-LPC | 35.68 ± 1.13 | 32.11 ± 1.15* | 36.61 ± 1.42* | 37.90 ± 1.20* | 5.79 ± 1.08 |
| LPC-DW286 | 35.90 ± 1.13 | 32.28 ± 1.27* | 36.24 ± 1.66* | 37.44 ± 2.15* | 5.17 ± 1.24 |
| DW286 | 36.84 ± 1.83 | 33.02 ± 1.95* | 37.46 ± 1.96* | 38.61 ± 1.95** | 5.59 ± 1.03 | n = 9; (Mean ± S.D.), g;
[1] Overnight fasted;
[2] Body weight gains during 2 days after dosing;
*$p < 0.01$ and
**$p < 0.05$ compared to that of intact control by MW test.

9-3. Changes on the Organ Weights of CPA-Treated Model

Significantly ($p<0.01$) decreases on the relative and absolute spleen and thymus weights were detected in CPA control compared to that of intact control. However, non-significantly increases in the thymic weights were detected in LPC, Mix and DW286, and significantly ($p<0.01$) increases of spleen weights were detected in LPC, Mix and DW286-LPC groups compared to that of CPA control, respectively (Table 15).

TABLE 15

Changes of absolute and relative organ weights detected in CPA-treated mice

| Organ Weight | Thymus Absolute (g) | Relative (%) | Spleen Absolute (g) | Relative (%) |
|---|---|---|---|---|
| Controls | | | | |
| Intact | 0.074 ± 0.010 | 0.178 ± 0.023 | 0.133 ± 0.026 | 0.322 ± 0.061 |
| CPA | 0.033 ± 0.008* | 0.084 ± 0.019* | 0.049 ± 0.009* | 0.127 ± 0.022* |
| Test groups | | | | |
| LPC | 0.037 ± 0.007* | 0.099 ± 0.017* | 0.066 ± 0.007*,# | 0.178 ± 0.018*,# |
| Mix | 0.036 ± 0.008* | 0.096 ± 0.021* | 0.063 ± 0.009*,# | 0.168 ± 0.023*,# |

TABLE 15-continued

Changes of absolute and relative organ weights detected in CPA-treated mice

| Organ Weight | Thymus | | Spleen | |
|---|---|---|---|---|
| | Absolute (g) | Relative (%) | Absolute (g) | Relative (%) |
| DW286-LPC | 0.035 ± 0.012* | 0.093 ± 0.032* | 0.064 ± 0.008*,# | 0.168 ± 0.021*,# |
| LPC-DW286 | 0.033 ± 0.007* | 0.089 ± 0.018* | 0.054 ± 0.008* | 0.145 ± 0.015* |
| DW286 | 0.032 ± 0.008* | 0.082 ± 0.018* | 0.045 ± 0.009* | 0.117 ± 0.023* | n = 9; (Mean ± S.D.), g or %; Relative weight (%) = [(Absolute organ weights/Body weight at sacrifice) × 100];

*$p < 0.01$ compared to that of intact control by MW test;

$p < 0.01$ compared to that of CPA control by MW test.

The absolute and relative thymic weights in CPA control were showed −55.74 and −52.62% changes compared to that of intact control, respectively. The absolute thymic weights in LPC, Mix, DW286-LPC, LPC-DW286 and DW286 groups were changed as 13.31, 10.24, 7.17, 2.39 and −2.73%, and the relative thymic weights were changed as 17.56, 13.74, 9.51, 5.47 and −3.12% compared to that of CPA control, respectively.

The absolute and relative splenic weights in CPA control were showed −63.38 and −60.63% changes compared to that of intact control, respectively. The absolute splenic weights in LPC, Mix, DW286-LPC, LPC-DW286 and DW286 groups were changed as 35.62, 28.77, 31.28, 11.87 and −7.08%, and the relative splenic weights were changed as 40.69, 32.54, 32.96, 14.38 and −7.46% compared to that of CPA control, respectively.

It was thought that the decreases in splenic and thymic weights in all the CPA dosing groups result from the reduction of lymphocytes. It was observed that DW286-LPC combination and LPC effectively inhibited the decreases in the lymphoid organ weight induced by CPA dosing. Similar or relatively lower effects of inhibiting the decreases were exhibited in the Mix and LPC-DW286 groups as compared with the LPC alone group.

9-4. Changes on the Total Blood WBC Numbers in CPA-Treated Model

Significantly ($p<0.01$) decrease on the total WBC numbers were detected in CPA control compared to that of intact control. However, non-significantly increases in the total WBC numbers were detected in all dosing groups except for DW286 group, and especially a significantly ($p<0.01$) increase was detected in DW286-LPC group compared to that of CPA control (table 16).

TABLE 16

Changes of blood WBC numbers and their differential counts detected in CPA-treated mice

| Blood WBC | Controls | | Test groups | | | | |
|---|---|---|---|---|---|---|---|
| | Intact | CPA | LPC | Mix | DW286-LPC | LPC-DW286 | DW286 |
| Total WBC (×10³/mm³) | 5.54 ± 2.17 | 0.47 ± 0.13* | 0.58 ± 0.14* | 0.62 ± 0.19* | 0.75 ± 0.28*,## | 0.56 ± 0.10*,# | 0.41 ± 0.19* |
| Differentials (%) | | | | | | | |
| Neutrophils | 22.33 ± 5.57 | 42.01 ± 13.88* | 20.56 ± 8.76# | 22.67 ± 3.94# | 21.00 ± 6.82# | 34.11 ± 5.84* | 41.56 ± 10.64* |
| Monocytes | 6.78 ± 1.30 | 37.71 ± 25.46* | 5.56 ± 3.13# | 6.67 ± 2.74## | 3.33 ± 2.06*,# | 5.11 ± 2.15**,# | 42.78 ± 17.33* |
| Basophils | 0.56 ± 0.73 | 1.06 ± 1.71 | 2.33 ± 1.22*,## | 2.67 ± 2.00**,## | 1.00 ± 0.71 | 1.11 ± 0.93 | 0.89 ± 0.78 |
| Eosinophils | 1.17 ± 1.65 | 0.17 ± 0.51 | 1.33 ± 1.12## | 2.33 ± 1.32# | 0.33 ± 0.50 | 1.78 ± 1.20# | 0.22 ± 0.44 |
| Lymphocytes | 69.17 ± 4.61 | 19.04 ± 30.10* | 70.22 ± 9.90# | 65.67 ± 7.57# | 74.33 ± 8.15# | 57.89 ± 5.21*,# | 14.56 ± 9.75* | n = 9;

(Mean ± S.D.), ×10³/mm³ or %,

*$p < 0.01$ and **$p < 0.05$ compared to that of intact control by MW test,

$p < 0.01$ and ##$p < 0.05$ compared to that of CPA control by MW test.

The blood total WBC numbers in CPA control were showed −91.58% changes compared to that of intact control. They were changed in LPC, Mix, DW286-LPC, LPC-DW286 and DW286 groups were changed as 25.00, 32.74, 61.31, 19.64 and −11.31% compared to that of CPA control, respectively. That is, significant decreases in the WBC number are generally known to result from CPA dosing. However, as a result of this experiment, it was observed that LPC relatively effectively inhibited the decreases in the WBC number induced by CPA dosing, and more favorable effects were exhibited in the DW286-LPC group as compared with the LPC alone group. These results indicate that the pre-dosing of DW286 has more favorable effects when combinational agents are used.

9-5. Changes on the Differential Counts of WBC in CPA-Treated Model

Dramatical decrease on the blood lymphocytes were detected in CPA control compared to that of intact control, and accordingly, the ratio of neutophils and monocytes were increased. However, these changes on the WBC differential counts were significantly (p<0.01) reduced in all dosing groups except for DW286 group, respectively. Especially, more favorable effects were detected in DW286-LPC group than that of LPC group (Table 16).

The ratio of lymphocytes, neutrophils and monocytes in CPA control were showed −72.47, 88.11 and 456.43% changes compared to those of intact control, respectively. The ratio of lymphocytes in LPC, Mix, DW286-LPC, LPC-DW286 and DW286 groups were changed as 268.78, 244.85, 290.37, 204.01 and −23.56%, ratio of neutrophils were changed as −51.07, −46.05, −50.01, −18.81 and −1.09%, and the ratio of monocytes were changed as −85.27, −82.32, −91.16, −86.45 and 13.43% compared to that of CPA control, respectively.

9-6. Changes on the Bone Marrow MNPCEs in CPA-Treated Model

Significantly (p<0.01) increases in the MNPCEs and decreases in the PCE/(PCE+NCE) were detected in CPA control compared to that of intact control, respectively. No meaningful changes in the bone marrow MNPCEs and PCE/(PCE+NCE) were detected in all dosing group in the present study (table 17).

The bone marrow MNPCEs and PCE/(PCE+NCE) in CPA control were showed 1512.50 and −60.38% changes compared to that of intact control, respectively. The MNPCE numbers in LPC, Mix, DW286-LPC, LPC-DW286 and DW286 groups were changed as −14.34, −0.78, −12.02, −5.43 and −10.85%, and the PCE/(PCE+NCE) were changed as −12.98, 6.14, −11.80, −1.49 and −14.79% compared to that of CPA control, respectively.

These results support that LPC and DW286 both alone and in combination have little effect on the increase in the number of bone marrow MNPCEs due to CPA. The MNPCE ratio is an index for evaluating cytotoxicity of test materials in bone marrows. As a result of this study, significant decreases in the PCE ratio were detected in all the CPA dosing groups. These decreases in the PCE ratio are determined to be due to overdosing of CPA.

9-7. Histopathogy of Thymus and Spleen in CPA-Treated Model

Figure 7:
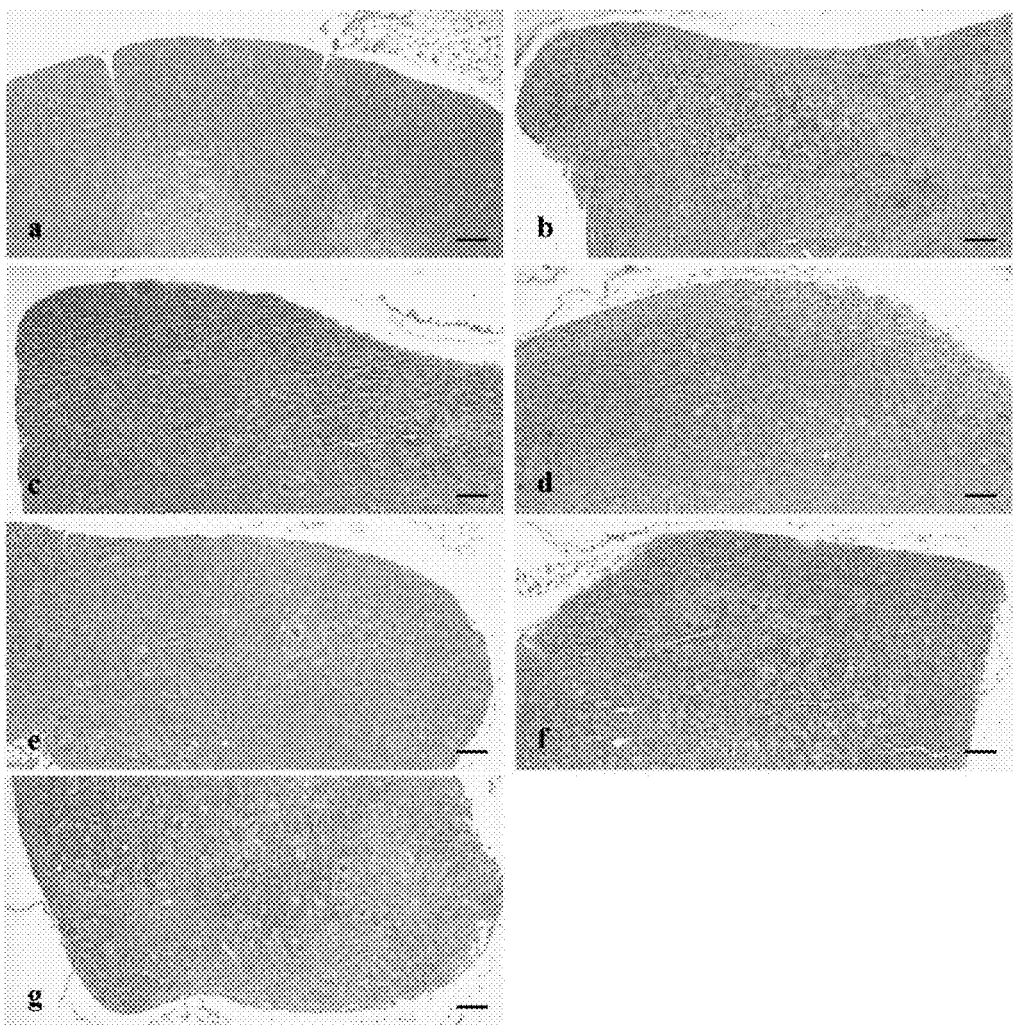
FIG. 7 shows histopathological profiles of thymus detected in the INTACT control (a), CPA control (b), LPC (c), Mix (d), DW286-LPC (e), LPC-DW286 (f), and DW285 (g) groups in the CPA-treated model. Decreases in lymphoid cells in the thymic cortex were detected in the CPA control group. However, the atrophic changes were effectively inhibited by treatment of the LPC, LPC-DW286, and DW286-LPC groups, and the DW286-LPC group showed the highest inhibition trend as compared with other groups.
Figure 8:
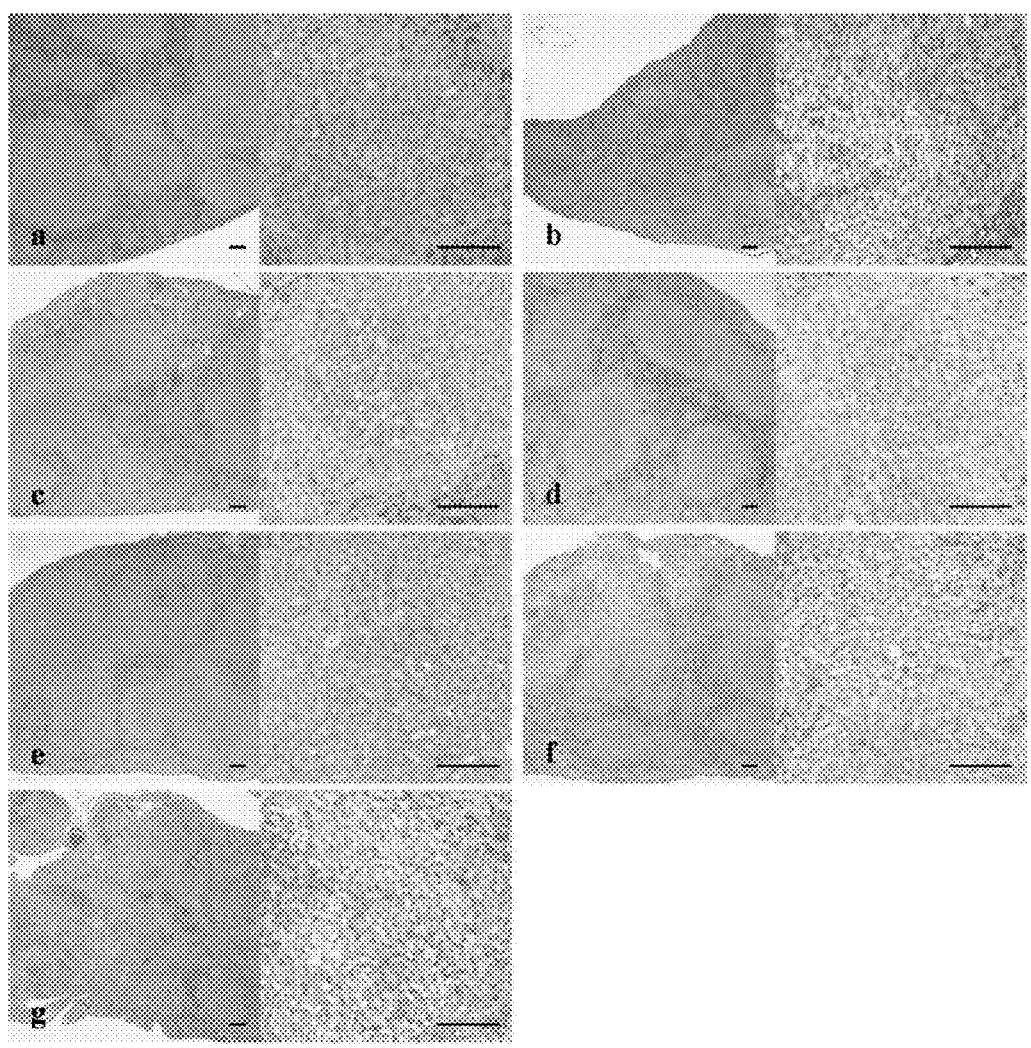
FIG. 8 shows histopathological profiles of spleen detected in the INTACT control (a), CPA control (b), LPC (c), Mix (d), DW286-LPC (e), LPC-DW286 (f), and DW285 (g) groups in the CPA-treated model. Dramatical splenic atrophy and decrease in lymphoid cells were detected in the CPA control group. However, these atrophic changes were effectively inhibited by treatment of the LPC, LPC-DW286, and DW286-LPC groups, and the DW286-LPC group showed the highest inhibition trend as compared with other groups.
Figure 9:
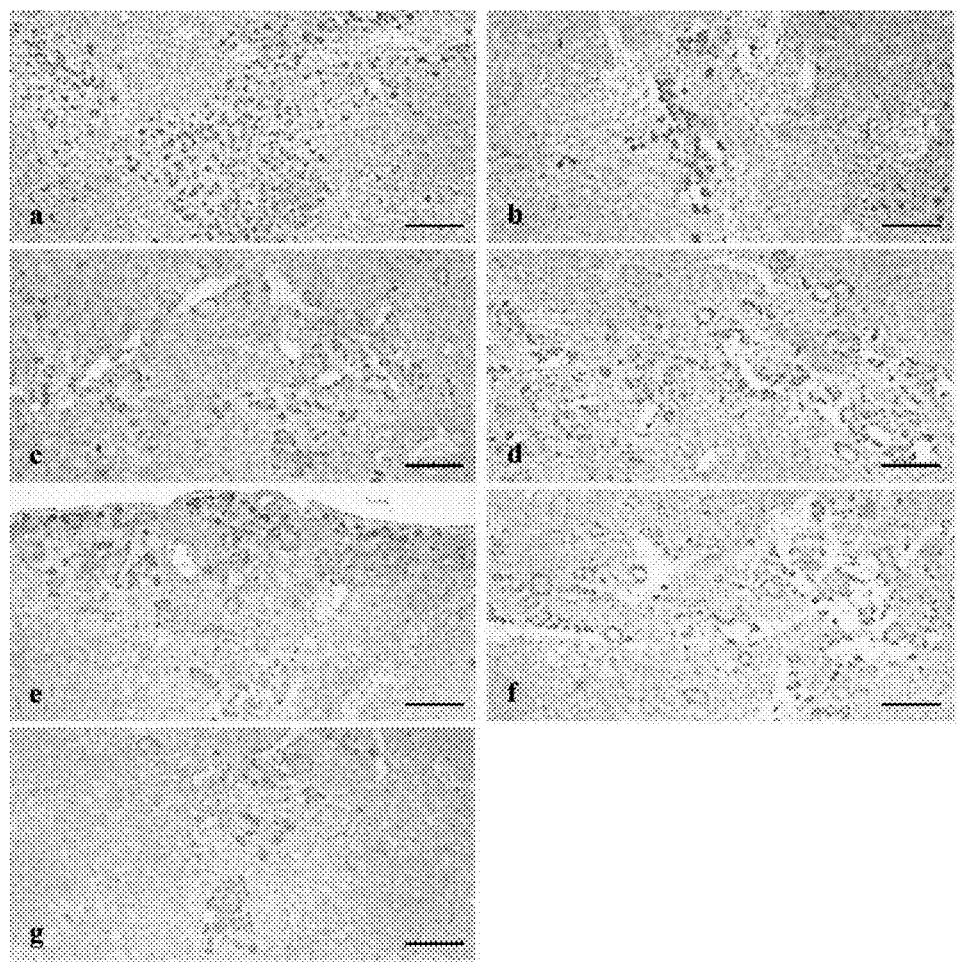
FIG. 9 shows changes in splenic CD3+ cells in the INTACT control (a), CPA control (b), LPC (c), Mix (d), DW286-LPC (e), LPC-DW286 (f), and DW285 (g) groups in the CPA-treated model. Dramatical decreases in splenic CD3+ cells were detected in the CPA control group as compared with the INTACT control group. However, these decreases were effectively inhibited in all the dosing groups as compared with the CPA control group except for the DW286 group, respectively. Especially, similar or slightly more favorable effects were detected in the DW286-LPC group as compared with the LPC group.
Figure 10:
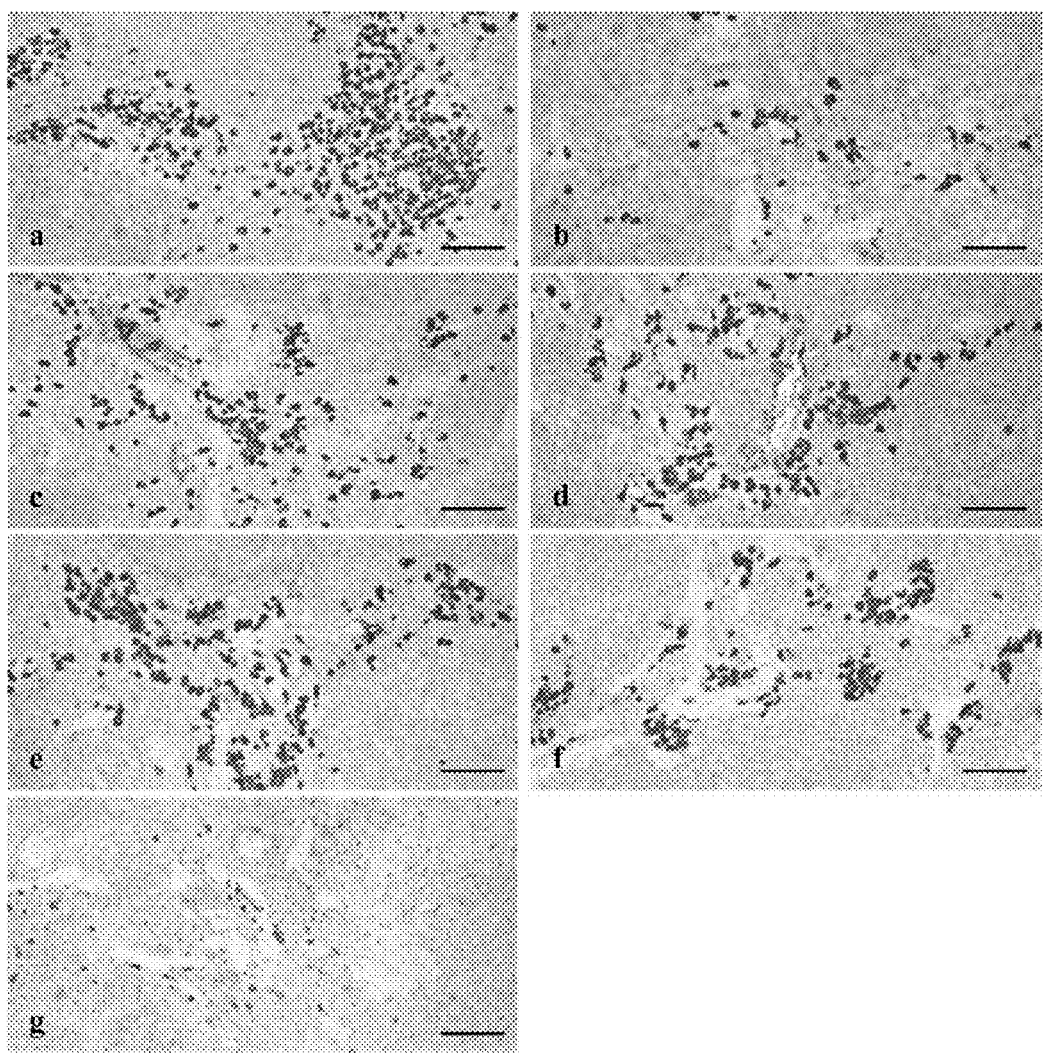
FIG. 10 shows changes in splenic CD4+ cells in the INTACT control (a), CPA control (b), LPC (c), Mix (d), DW286-LPC (e), LPC-DW286 (f), and DW285 (g) groups in the CPA-treated model. Dramatical decreases in splenic CD3+ cells were detected in the CPA control group as compared with the INTACT control group. However, these decreases were effectively inhibited in all the dosing groups as compared with the CPA control group except for the DW286 group, respectively. Especially, similar or slightly more favorable effects were detected in the DW286-LPC group as compared with the LPC group.
Figure 11:
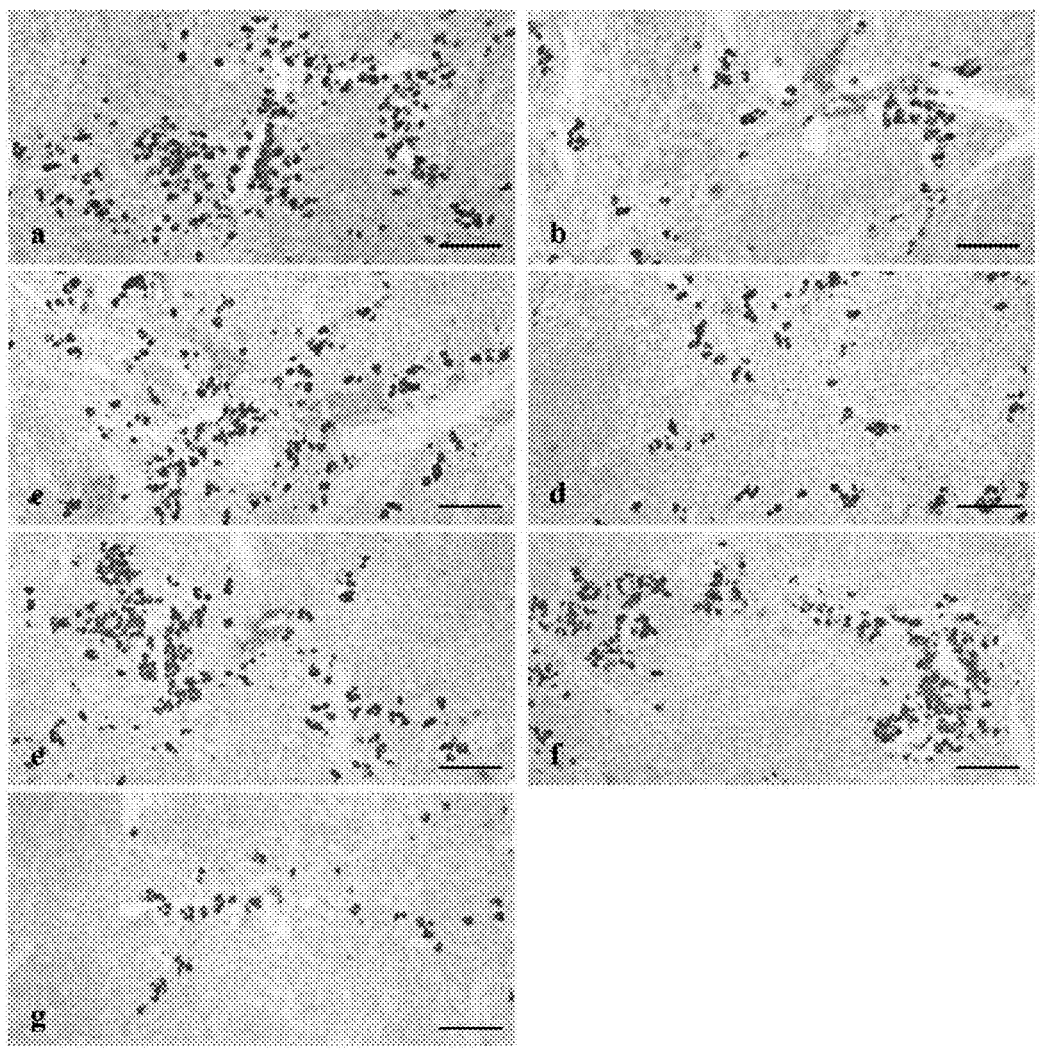
FIG. 11 shows changes in splenic CD8+ cells in the INTACT control (a), CPA control (b), LPC (c), Mix (d), DW286-LPC (e), LPC-DW286 (f), and DW285 (g) groups in the CPA-treated model. Dramatical decreases in splenic CD3+ cells were detected in the CPA control group as compared with the INTACT control group. However, these decreases were effectively inhibited in all the dosing groups as compared with the CPA control group except for the DW286 group, respectively. Especially, similar or slightly more favorable effects were detected in the DW286-LPC group as compared with the LPC group.
Figure 12:
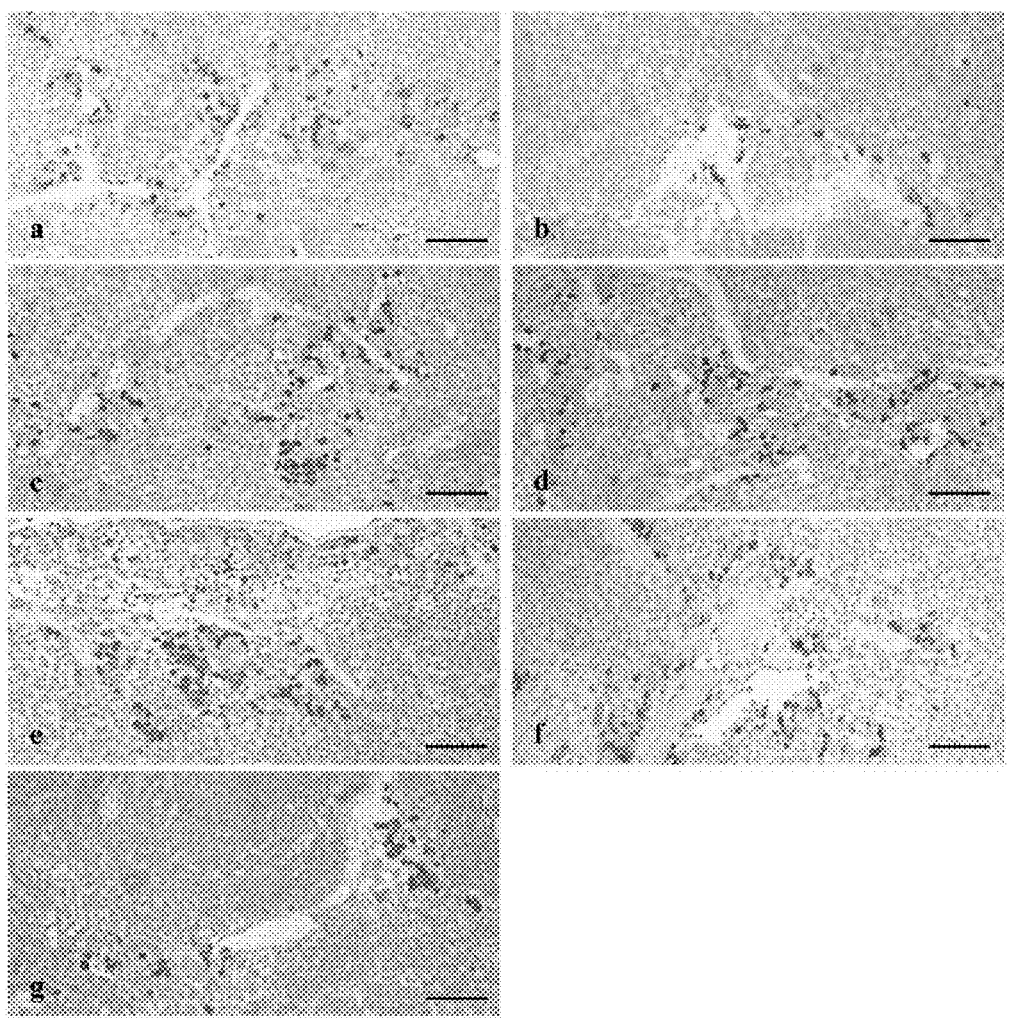
FIG. 12 shows changes in splenic TNF-α cells in the INTACT control (a), CPA control (b), LPC (c), Mix (d), DW286-LPC (e), LPC-DW286 (f), and DW285 (g) groups in the CPA-treated model. Dramatical decreases in splenic CD3+ cells were detected in the CPA control group as compared with the INTACT control group. However, these decreases were effectively inhibited in all the dosing groups as compared with the CPA control group except for the DW286 group, respectively. Especially, similar or slightly more favorable effects were detected in the DW286-LPC group as compared with the LPC group.
Figure 13:
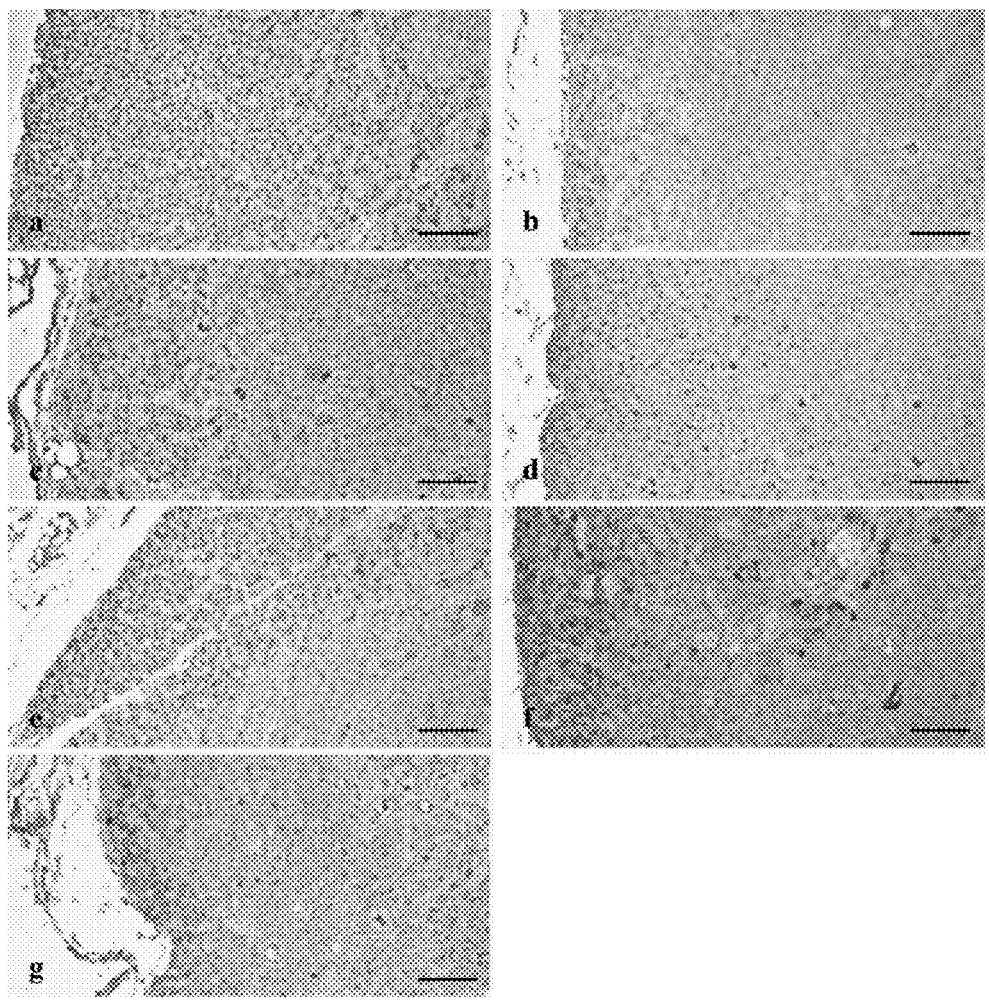
FIG. 13 shows changes in thymic CD3+ cells in the INTACT control (a), CPA control (b), LPC (c), Mix (d), DW286-LPC (e), LPC-DW286 (f), and DW285 (g) groups in the CPA-treated model. Dramatical decreases in thymic CD3+ cells were detected in the CPA control group as compared with the INTACT control group. However, these decreases were effectively inhibited in all the dosing groups as compared with the CPA control group except for the DW286 group, respectively. Especially, similar or slightly more favorable effects were detected in the DW286-LPC group as compared with the LPC group.
Figure 14:
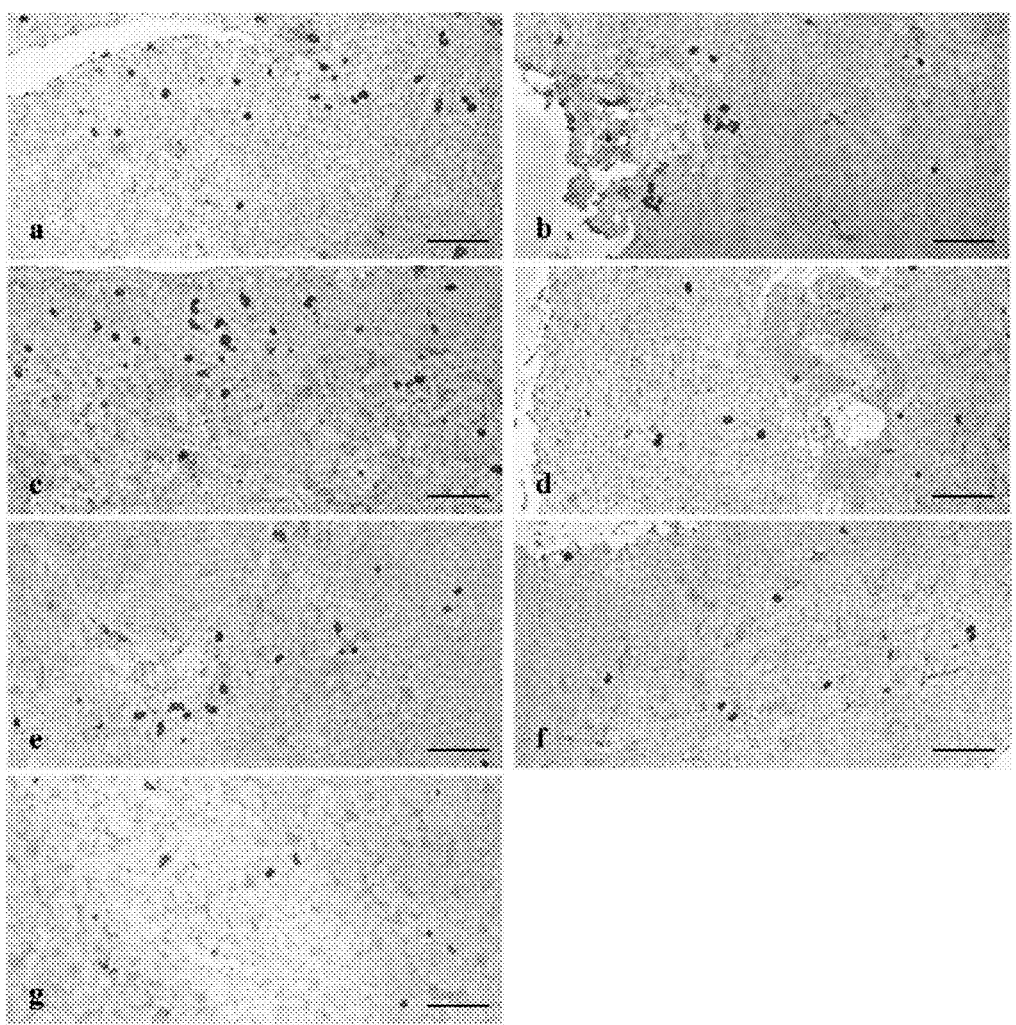
FIG. 14 shows changes in thymic CD4+ cells in the INTACT control (a), CPA control (b), LPC (c), Mix (d), DW286-LPC (e), LPC-DW286 (f), and DW285 (g) groups in the CPA-treated model. Dramatical decreases in thymic CD4+ cells were detected in the CPA control group as compared with the INTACT control group. However, these decreases were effectively inhibited in all the dosing groups as compared with the CPA control group except for the DW286 group, respectively. Especially, similar or slightly more favorable effects were detected in the DW286-LPC group as compared with the LPC group.
Figure 15:
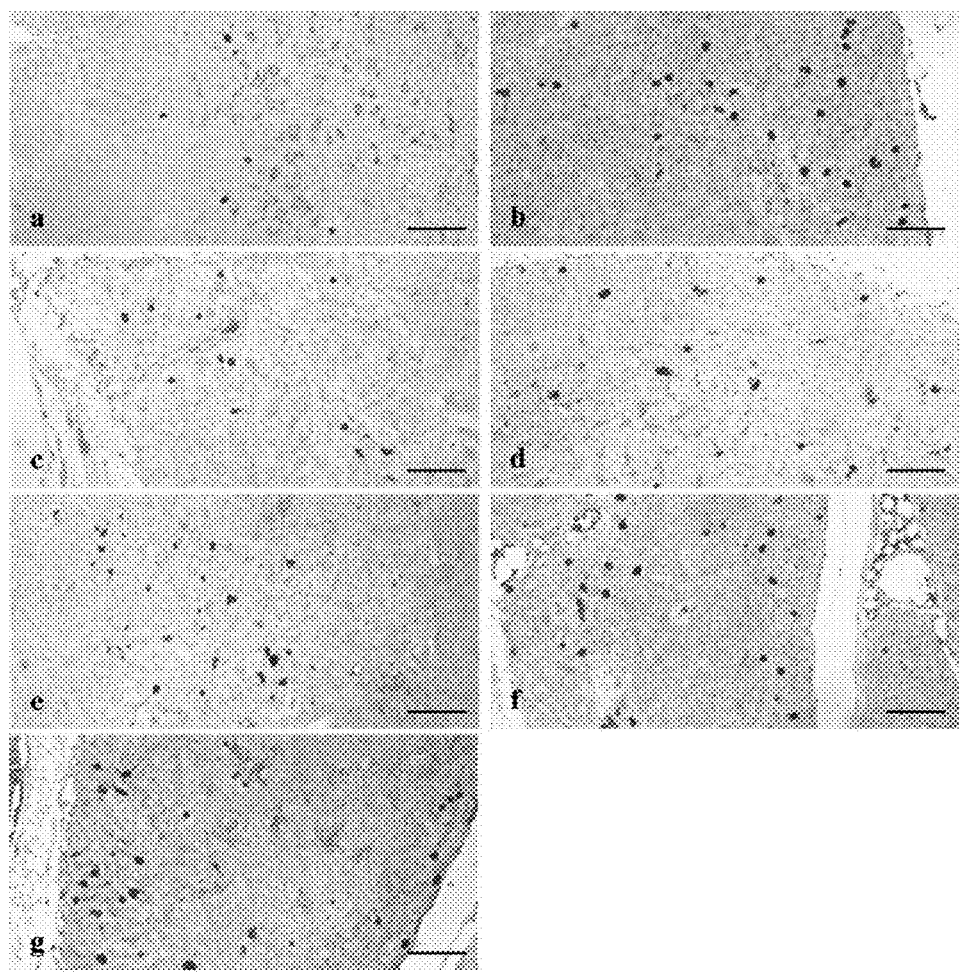
FIG. 15 shows changes in thymic CD8+ cells in the INTACT control (a), CPA control (b), LPC (c), Mix (d), DW286-LPC (e), LPC-DW286 (f), and DW285 (g) groups in the CPA-treated model. Dramatical decreases in thymic CD8+ cells were detected in the CPA control group as compared with the INTACT control group. However, these decreases were effectively inhibited in all the dosing groups as compared with the CPA control group except for the DW286 group, respectively. Especially, similar or slightly more favorable effects were detected in the DW286-LPC group as compared with the LPC group.
Figure 16:
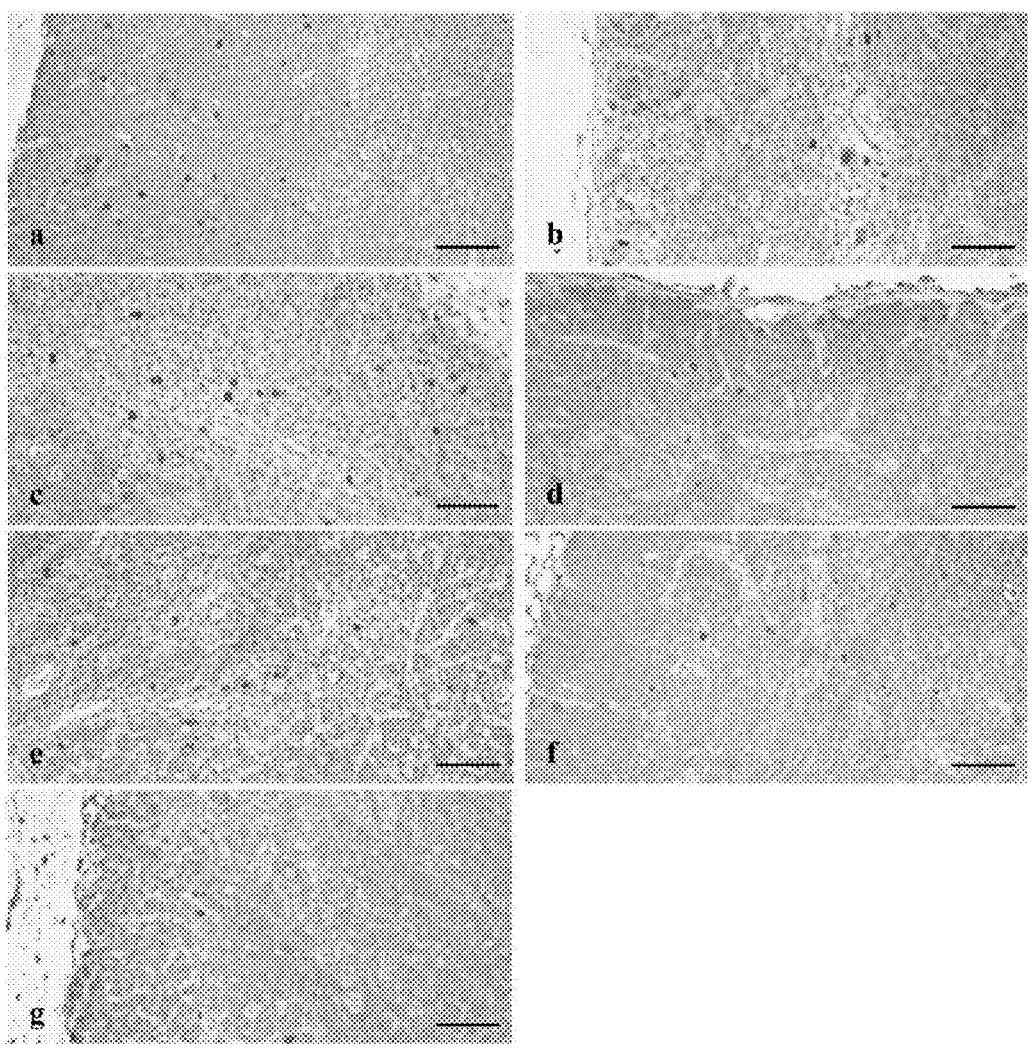
FIG. 16 shows changes in thymic TNF-α cells in the INTACT control (a), CPA control (b), LPC (c), Mix (d), DW286-LPC (e), LPC-DW286 (f), and DW285 (g) groups in the CPA-treated model. Dramatical decreases in thymic TNF-α cells were detected in the CPA control group as compared with the INTACT control group. However, these decreases were effectively inhibited in all the dosing groups as compared with the CPA control group except for the DW286 group, respectively. Especially, similar or slightly more favorable effects were detected in the DW286-LPC group as compared with the LPC group.

Dramatical splenic atrophy and decrease of lymphoid cells in the thymic cortex were detected in CPA control. However, these atrophic changes were effectively inhibited by treatment of LPC, LPC-DW286, and DW286-LPC and the DW286-LPC group showed the highest inhibition trends compared to those of other groups (FIGS. 7 and 8). At histomorphometry, the number of white pulps in spleen were significantly (p<0.01) increased in CPA control compared that of intact control, the white pulp numbers were significantly (p<0.01) increased in all dosing groups compared to that of CPA control except for DW286 group. In addition, the incidences of decrease of lymphoid cells in the thymic cortex were also dramatically inhibited in all dosing groups except for DW286 group compared to that of CPA control, respectively (table 18).

TABLE 18

Changes of histomorphometry of spleen and thymus detected in CPA-treated mice at histopathology

| Histopathology | Spleen: Number of white pulps[1] | Thymus: Incidences of thymic cortex atrophy[2] |
|---|---|---|
| Controls | | |
| Intact | 18.67 ± 2.12 | 0/9 (0%) |
| CPA | 6.22 ± 1.20* | 9/9 (100%) |

TABLE 17

Clanges of bone marrow MNPCE and PCE/(NCE + PCE) detected in CPA-treated mice

| Bone Marrow | Among 1000 PCEs | Among 500 erythrocytes | | |
|---|---|---|---|---|
| | % MNPCE | PCE | NCE | PCE/(NCE + PCE) |
| Controls | | | | |
| Intact | 0.18 ± 0.08 | 356.44 ± 34.14 | 143.56 ± 34.13 | 0.71 ± 0.07 |
| CPA | 2.87 ± 0.35* | 141.22 ± 35.12* | 358.78 ± 35.12* | 0.28 ± 0.07* |
| Test groups | | | | |
| LPC | 2.46 ± 0.75* | 122.89 ± 22.32* | 377.11 ± 22.32* | 0.25 ± 0.04* |
| Mix | 2.84 ± 0.79* | 149.89 ± 41.78* | 350.11 ± 41.78* | 0.30 ± 0.08* |
| DW286-LPC | 2.52 ± 0.65* | 124.56 ± 27.80* | 375.44 ± 27.80* | 0.25 ± 0.06* |
| LPC-DW286 | 2.71 ± 0.69* | 139.11 ± 35.74* | 360.89 ± 35.74* | 0.28 ± 0.07* |
| DW286 | 2.56 ± 0.57* | 120.33 ± 17.07* | 379.67 ± 17.07* | 0.24 ± 0.03* | n = 9; (Mean ± S.D.);
*p < 0.01 compared to that of intact control by MW test.

TABLE 18-continued

Changes of histomorphometry of spleen and thymus detected in CPA-treated mice at histopathology

| Histopathology | Spleen: Number of white pulps[1] | Thymus: Incidences of thymic cortex atrophy[2] |
|---|---|---|
| Test groups | | |
| LPC | 12.56 ± 1.81*,# | 8/9 (88.89%) |
| Mix | 10.67 ± 1.58*,# | 8/9 (88.89%) |
| DW286-LPC | 12.78 ± 1.39*,# | 6/9 (66.67%) |
| LPC-DW286 | 12.56 ± 1.67*,# | 7/9 (77.78%) |
| DW286 | 6.11 ± 1.45* | 9/9 (100%) | n = 9, (Mean ± S.D.);
[1]N/histological sections;
[2]The numbers of atrophic changes on thymic cortex/total observed number of thymus (% of observation);
*$p < 0.01$ compared to that of intact control by MW test;
$p < 0.01$ compared to that of CPA control by MW test.

The numbers of white pulps of spleen in CPA control were showed −66.67% changes compared to that of intact control. They were changed in LPC, Mix, DW286-LPC, LPC-DW286 and DW286 groups were changed as 101.79, 71.43, 105.36, 101.79 and −1.79% compared to that of CPA control, respectively.

1. The incidences of decrease of lymphoid cells in the thymic cortex in intact control, CPA control, LPC, Mix, DW286-LPC, LPC-DW286 and DW286 groups were detected as 0, 100, 88.89, 88.89, 66.67, 77.78 and 100%, respectively.

As a result of this experiment, it was observed that DW286-LPC combination and LPC effectively inhibited the decrease in the number of lymphocytes in the lymphoid organ, and more favorable effects were detected in the DW286-LPC group as compared with the LPC alone group.

9-8. IHC of Thymus and Spleen in CPA-Treated Model

Significantly ($p<0.01$) decreases of splenic CD3+, CD4+, CD8+ and TNF-α+ cells were detected in CPA control compared to that of intact control, and also the significantly ($p<0.01$) decreases of CD3+ and TNF-α+ cells were detected in cortex and medulla of thymus, respectively. However, these cells were significantly ($p<0.01$ or $p<0.05$) increased in all dosing groups compared to that of CPA control except for DW286 group, respectively in the both thymus and spleen. Especially similar or slightly more favorable effects were detected in DW286-LPC group compared to those of LPC group (table 19 and FIG. 9-16).

TABLE 19

Changes on histomorphometry of CD3+, CD4+, CD8+ and TNF-α+ cells in the spleen and thymus detected in CPA-treated mice at immunohistochemistry

| IHC-Histo-morphometry | Controls | | Test groups | | | | |
|---|---|---|---|---|---|---|---|
| | Intact | CPA | LPC | Mix | DW286-LPC | LPC-DW286 | DW286 |
| Spleen | | | | | | | |
| CD3+ cells | 177.22 ± 31.99 | 65.00 ± 13.18* | 76.89 ± 6.23*,## | 155.22 ± 14.70*,# | 129.56 ± 18.64*,# | 117.67 ± 19.35*,# | 55.89 ± 14.70* |
| CD4+ cells | 274.33 ± 19.43 | 46.22 ± 12.89* | 109.33 ± 20.77*,# | 92.33 ± 6.82*,# | 108.89 ± 10.97*,# | 83.11 ± 8.96*,# | 41.22 ± 13.74* |
| CD8+ cells | 191.56 ± 14.88 | 51.22 ± 13.55* | 88.56 ± 11.18*,# | 76.22 ± 10.00*,# | 107.22 ± 27.53*,# | 71.11 ± 9.92*,# | 45.78 ± 11.21* |
| TNF-α+ cells | 96.44 ± 18.82 | 46.56 ± 12.29* | 63.67 ± 9.10*,# | 52.56 ± 16.71* | 62.78 ± 9.93*,## | 59.44 ± 9.45*,## | 40.11 ± 12.34* |
| Thymus: Cortex | | | | | | | |
| CD3+ cells | 740.22 ± 92.10 | 182.00 ± 57.65* | 780.22 ± 85.78# | 576.22 ± 38.94*,# | 770.67 ± 107.98# | 691.44 ± 88.43# | 165.33 ± 47.02* |
| CD4+ cells | 1.56 ± 0.73 | 2.56 ± 1.59 | 13.00 ± 2.45*,# | 3.22 ± 1.39* | 2.89 ± 1.05** | 3.11 ± 1.27** | 3.11 ± 1.69** |
| CD8+ cells | 2.33 ± 2.24 | 3.00 ± 1.73 | 3.33 ± 1.22** | 4.00 ± 1.66** | 2.78 ± 1.30 | 3.33 ± 1.50 | 4.00 ± 2.74 |
| TNF-α+ cells | 5.22 ± 1.56 | 2.65 ± 1.13* | 4.22 ± 1.20** | 3.33 ± 0.87* | 4.11 ± 1.17## | 3.33 ± 0.71* | 2.22 ± 0.97* |
| Thymus: Medulla | | | | | | | |
| CD3+ cells | 3.33 ± 1.00 | 0.33 ± 0.50* | 41.89 ± 10.23*,# | 2.00 ± 1.00**,# | 8.22 ± 3.31*,# | 8.65 ± 3.78*,# | 0.22 ± 0.44* |
| CD4+ cells | 2.67 ± 0.71 | 2.44 ± 0.88 | 2.22 ± 0.97 | 2.00 ± 0.71 | 2.11 ± 0.60 | 2.56 ± 1.42 | 1.78 ± 0.67** |
| CD8+ cells | 1.56 ± 0.73 | 2.00 ± 0.71 | 1.89 ± 0.60 | 1.78 ± 0.67 | 1.89 ± 0.60 | 1.67 ± 0.71 | 1.56 ± 0.73 |
| TNF-α+ cells | 1.56 ± 0.73 | 0.00 ± 0.00* | 1.33 ± 1.00* | 0.00 ± 0.00* | 0.00 ± 0.00* | 1.33 ± 0.50# | 0.00 ± 0.00* | n = 9;
(Mean ± S.D.), N/1000 splenocytes or thymocytes;
*$p < 0.01$ and **$p < 0.05$ compared to that of intact control by MW test;
$p < 0.01$ and ##$p < 0.05$ compared to the of CPA control by MW test.

The numbers of splenic CD3+, CD4+ and CD8+ cells in CPA control were showed −68.32, −83.15 and −73.26% changes compared to those of intact control, respectively. The numbers of CD3+ cells in LPC, Mix, DW286-LPC, LPC-DW286 and DW286 groups were changed as 18.29, 77.26, 99.32, 81.03 and −14.02%, the numbers of CD4+ cells were changed as 136.54, 99.76, 135.58, 79.81 and −10.82%, and the numbers of CD8+ cells were changed as 72.89, 48.81, 109.33, 38.83 and −10.63% compared to that of CPA control, respectively.

The numbers of thymic cortex CD3+, CD4+ and CD8+ cells in CPA control were showed −75.41, 64.29 and 28.57% changes compared to those of intact control, respectively. The numbers of CD3+ cells in LPC, Mix, DW286-LPC, LPC-DW286 and DW286 groups were changed as 328.69, 216.61, 323.44, 279.91 and −9.16%, the numbers of CD4+ cells were changed as 408.70, 26.09, 13.04, 31.74 and 21.74%, and the numbers of CD8+ cells were changed as 11.11, 33.33, −7.41, 11.11 and 33.33% compared to that of CPA control, respectively.

The numbers of thymic medulla CD3+, CD4+ and CD8+ cells in CPA control were showed −90.00, −8.33 and 28.57% changes compared to those of intact control, respectively. The numbers of CD3+ cells in LPC, Mix, DW286-LPC, LPC-DW286 and DW286 groups were changed as 12466.67, 500.00, 2366.67, 2466.67 and −33.33%, the numbers of CD4+ cells were changed as −9.09, −18.18, −13.64, 4.55 and 27.27%, and the numbers of CD8+ cells were changed as −5.56, −11.11, −5.56, −16.67 and −22.22% compared to that of CPA control, respectively.

The numbers of splenic, thymic cortex and medulla TNF-α+ cells in CPA control were showed −51.73, −51.06 and −155.56% changes compared to those of intact control, respectively. The splenic TNF-α+ cells in LPC, Mix, DW286-LPC, LPC-DW286 and DW286 groups were changed as 36.75, 12.89, 34.84, 27.68 and −13.840, the thymic cortex TNF-α+ cells were changed as 65.22, 30.43, 60.87, 30.43 and −13.040, and the thymic medulla TNF-α+ cells were changed as 133.33, 0.00, 0.00, 133.33 and 0.00% compared to that of CPA control, respectively. That is, CPA caused significant decreases in the number of CD3+, CD4+, CD8+, and TNF-α+ cells in spleen and thymus. However, it was observed that DW286-LPC combination and LPC effectively inhibited the decreases of the number of these cells induced by CPA dosing, and more favorable effects were observed in the DW286-LPC group as compared with the LPC alone group.

It was observed that LPC alone and LPC and DW286 in combination comparatively effectively inhibited deaths due to CPA-induced immunosuppression and CPA-CLP-induced sepsis, and the most favorable effect was detected in the DW286 pre-dosing and then LPC dosing regime (DW286-LPC group).

The above results support that remarkable effects in enhancement of immunity and treatment of bacterial infections can be exhibited when LPC of the present invention in combination with various antibiotics are simultaneously or sequentially dosed than when LPC alone is dosed.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

The invention claimed is:

1. A method for treating sepsis comprising administering to a subject in need thereof L-α-lysophosphatidylcholine stearoyl and an antibiotic selected from the group consisting of DW286 (7-[3-(aminomethyl)-4-(methoxyimino)-3-methyltetrahydro-1H-1-pyrrolyl]-1-cyclopropyl-6-fluoro-4-oxo-1,4-dihydro[1,8]naphthyridine-3-carboxylic acid hydrochloric acid salt), ciprofloxacin hydrochloride hydrate, ceftriaxone sodium, doripenem, vancomycin hydrochloride, tobramycin and fusidic acid.

2. The method of claim 1, wherein L-α-lysophosphatidylcholine stearoyl and the antibiotic are sequentially administered.

3. A method for enhancing immunity comprising administering to a subject in need thereof L-α-lysophosphatidylcholine stearoyl and an antibiotic selected from the group consisting of DW286 (7-[3-(aminomethyl)-4-(methoxyimino)-3-methyltetrahydro-1H-1-pyrrolyl]-1-cyclopropyl-6-fluoro-4-oxo-1,4-dihydro[1,8]naphthyridine-3-carboxylic acid hydrochloric acid salt), ciprofloxacin hydrochloride hydrate, ceftriaxone sodium, doripenem, vancomycin hydrochloride, tobramycin and fusidic acid.

4. The method of claim 3, wherein the antibiotic is DW286.

* * * * *